United States Patent
Marlière et al.

(10) Patent No.: US 9,453,244 B2
(45) Date of Patent: Sep. 27, 2016

(54) METHOD FOR PRODUCING A MONOALKENE BY ENZYMATIC CONVERSION OF AN ALKYL MONOESTER

(71) Applicants: Scientist of Fortune S.A., Luxembourg (LU); Global Bioenergies, Evry (FR)

(72) Inventors: Philippe Marlière, Mouscron (BE); Maria Anissimova, Nozay (FR); Mathieu Allard, Saint Vrain (FR)

(73) Assignees: Global Bioenergies, Evry (FR); Scientist of Fortune S.A., Luxembourg (LU)

( * ) Notice: Subject to any disclaimer, the term of this patent is extended or adjusted under 35 U.S.C. 154(b) by 0 days.

(21) Appl. No.: 14/411,510

(22) PCT Filed: Jun. 28, 2013

(86) PCT No.: PCT/EP2013/063657
§ 371 (c)(1),
(2) Date: Dec. 28, 2014

(87) PCT Pub. No.: WO2014/001517
PCT Pub. Date: Jan. 3, 2014

(65) Prior Publication Data
US 2015/0159177 A1    Jun. 11, 2015

(30) Foreign Application Priority Data

Jun. 29, 2012 (EP) .................................... 121743710

(51) Int. Cl.
| | |
|---|---|
| *C12P 5/02* | (2006.01) |
| *C12P 7/04* | (2006.01) |
| *C12N 9/10* | (2006.01) |
| *C12N 9/88* | (2006.01) |

(52) U.S. Cl.
CPC .............. *C12P 5/026* (2013.01); *C12N 9/1085* (2013.01); *C12N 9/88* (2013.01); *C12Y 402/03* (2013.01); *Y02P 20/52* (2015.11)

(58) Field of Classification Search
CPC ........ C12P 5/026; C12P 7/04; C12N 9/1229; C12N 9/88; C12Y 402/03
USPC ......................................... 435/166, 193, 157
See application file for complete search history.

(56) References Cited

FOREIGN PATENT DOCUMENTS

| | | |
|---|---|---|
| WO | 2008003078 A2 | 1/2008 |
| WO | 2013040383 A1 | 3/2013 |

OTHER PUBLICATIONS

Brandt, W. et al.: "Molecular and structural basis of metabolic diversity mediated by prenyldiphosphate converting enzymes" ,Phytochemistry, vol. 70, No. 15-16, Oct. 2009, pp. 1758-1775, XP026748839, p. 1759-1760, paragraph 1; figure 1, p. 1765, paragraph 4—p. 1771, paragraph 6; figures 7, 8, 12.
Degenhardt, J. et al.: "Monoterpene and sesquiterpene synthases and the origin of terpene skeletal diversity in plants",Phytochemistry, vol. 70, No. 15-16, Oct. 2009, pp. 1621-1637, XP026748826, p. 1633, paragraph 4.4.
Fukuda, H. et al. : "Microbial Production of C3- and C4-Hydrocarbons under Aerobic Conditions", Agricultural and Biological Chemistry, vol. 48, No. 6, 1984, pp. 1679-1682, XP008160622, the whole document.
Wheeler, C.J. & Croteau, R.: "Monoterpene Cyc 1 ases. stereoelectronic requirements for substrate binding and ionization", Journal of Biological Chemistry, vol. 262, No. 17, Jun. 15, 1987, pp. 8213-8219, XP002693395, the whole document.
Written Opinion in parent PCT application PCT/EP2013/063657, 2013.

*Primary Examiner* — Robert Mondesi
*Assistant Examiner* — Md. Younus Meah
(74) *Attorney, Agent, or Firm* — Michele M. Wales; InHouse Patent Counsel, LLC

(57) ABSTRACT

The present invention relates to a method for producing a monoalkene comprising the step of enzymatically converting an alkyl monoester. The conversion preferably makes use of an enzyme which belongs to the group of terpene synthases or to the family of prenyltransferases. Moreover, the present invention relates to the use of a terpene synthase or of a prenyltransferase for enzymatically converting an alkyl monoester into a monoalkene.

20 Claims, 3 Drawing Sheets

Figure 1:
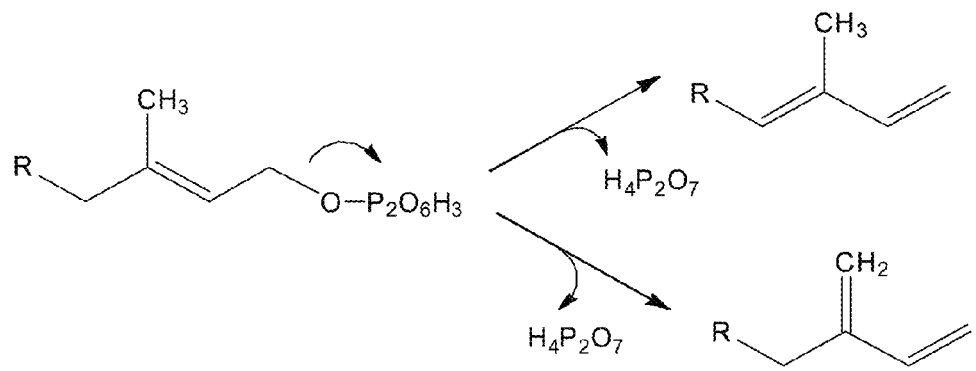
Figure 1:
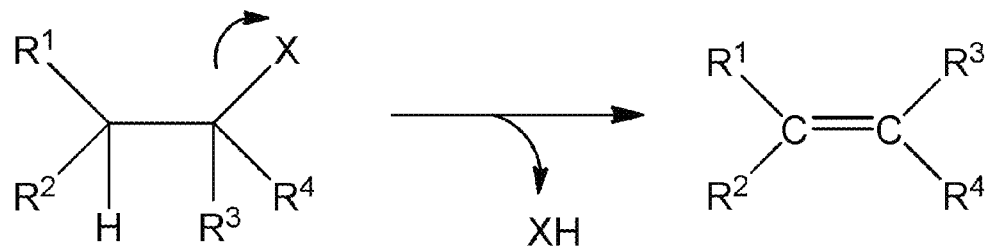

Natural reaction:

Target reaction:

SEQUENCE LISTING

<160> NUMBER OF SEQ ID NOS: 10

<210> SEQ ID NO 1
<211> LENGTH: 608

<212> TYPE: PRT
<213> ORGANISM: Pueraria montana var. lobata

<400> SEQUENCE: 1

```
Met Ala Thr Asn Leu Leu Cys Leu Ser Asn Lys Leu Ser Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                  45

Ser Ser Gln Phe Thr Gln Ile Thr Glu His Asn Ser Arg Arg Ser Ala
    50                  55                  60

Asn Tyr Gln Pro Asn Leu Trp Asn Phe Glu Phe Leu Gln Ser Leu Glu
65                  70                  75                  80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
    130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175

Arg Phe Lys Asp Lys Glu Gly Gly Phe Ser Gly Glu Leu Lys Gly Asp
            180                 185                 190

Val Gln Gly Leu Leu Ser Leu Tyr Glu Ala Ser Tyr Leu Gly Phe Glu
        195                 200                 205

Gly Glu Asn Leu Leu Glu Glu Ala Arg Thr Phe Ser Ile Thr His Leu
    210                 215                 220

Lys Asn Asn Leu Lys Glu Gly Ile Asn Thr Lys Val Ala Glu Gln Val
225                 230                 235                 240

Ser His Ala Leu Glu Leu Pro Tyr His Gln Arg Leu His Arg Leu Glu
                245                 250                 255

Ala Arg Trp Phe Leu Asp Lys Tyr Glu Pro Lys Glu Pro His His Gln
            260                 265                 270

Leu Leu Leu Glu Leu Ala Lys Leu Asp Phe Asn Met Val Gln Thr Leu
        275                 280                 285

His Gln Lys Glu Leu Gln Asp Leu Ser Arg Trp Trp Thr Glu Met Gly
    290                 295                 300

Leu Ala Ser Lys Leu Asp Phe Val Arg Asp Arg Leu Met Glu Val Tyr
305                 310                 315                 320

Phe Trp Ala Leu Gly Met Ala Pro Asp Pro Gln Phe Gly Glu Cys Arg
                325                 330                 335

Lys Ala Val Thr Lys Met Phe Gly Leu Val Thr Ile Ile Asp Asp Val
            340                 345                 350

Tyr Asp Val Tyr Gly Thr Leu Asp Glu Leu Gln Leu Phe Thr Asp Ala
        355                 360                 365

Val Glu Arg Trp Asp Val Asn Ala Ile Asn Thr Leu Pro Asp Tyr Met
    370                 375                 380

Lys Leu Cys Phe Leu Ala Leu Tyr Asn Thr Val Asn Asp Thr Ser Tyr
385                 390                 395                 400
```

-continued

Ser Ile Leu Lys Glu Lys Gly His Asn Asn Leu Ser Tyr Leu Thr Lys
            405                 410                 415

Ser Trp Arg Glu Leu Cys Lys Ala Phe Leu Gln Glu Ala Lys Trp Ser
            420                 425                 430

Asn Asn Lys Ile Ile Pro Ala Phe Ser Lys Tyr Leu Glu Asn Ala Ser
            435                 440                 445

Val Ser Ser Ser Gly Val Ala Leu Leu Ala Pro Ser Tyr Phe Ser Val
            450                 455                 460

Cys Gln Gln Gln Glu Asp Ile Ser Asp His Ala Leu Arg Ser Leu Thr
465                 470                 475                 480

Asp Phe His Gly Leu Val Arg Ser Ser Cys Val Ile Phe Arg Leu Cys
            485                 490                 495

Asn Asp Leu Ala Thr Ser Ala Ala Glu Leu Glu Arg Gly Glu Thr Thr
            500                 505                 510

Asn Ser Ile Ile Ser Tyr Met His Glu Asn Asp Gly Thr Ser Glu Glu
            515                 520                 525

Gln Ala Arg Glu Glu Leu Arg Lys Leu Ile Asp Ala Glu Trp Lys Lys
            530                 535                 540

Met Asn Arg Glu Arg Val Ser Asp Ser Thr Leu Leu Pro Lys Ala Phe
545                 550                 555                 560

Met Glu Ile Ala Val Asn Met Ala Arg Val Ser His Cys Thr Tyr Gln
            565                 570                 575

Tyr Gly Asp Gly Leu Gly Arg Pro Asp Tyr Ala Thr Glu Asn Arg Ile
            580                 585                 590

Lys Leu Leu Leu Ile Asp Pro Phe Pro Ile Asn Gln Leu Met Tyr Val
            595                 600                 605

<210> SEQ ID NO 2
<211> LENGTH: 601
<212> TYPE: PRT
<213> ORGANISM: Vitis vinifera

<400> SEQUENCE: 2

Met Ala Leu His Leu Phe Tyr Phe Pro Lys Gln Cys Phe Leu Thr His
1               5                   10                  15

Asn Leu Pro Gly His Pro Met Lys Lys Pro Pro Arg Gly Thr Thr Ala
            20                  25                  30

Gln Ile Arg Cys Ser Ala Asn Glu Gln Ser Phe Ser Leu Met Thr Glu
            35                  40                  45

Ser Arg Arg Ser Ala His Tyr Gln Pro Ala Phe Trp Ser Tyr Asp Phe
            50                  55                  60

Val Glu Ser Leu Lys Lys Arg Glu Glu Ile Cys Asp Gly Ser Val Lys
65                  70                  75                  80

Glu Leu Glu Lys Met Tyr Glu Asp Arg Ala Arg Lys Leu Glu Asp Glu
            85                  90                  95

Val Lys Trp Met Ile His Glu Lys Ser Ala Glu Pro Leu Thr Leu Leu
            100                 105                 110

Glu Phe Ile Asp Asp Ile Gln Arg Leu Gly Leu Gly His Arg Phe Glu
            115                 120                 125

Asn Asp Ile Lys Arg Ser Leu Asp Lys Ile Leu Leu Leu Glu Gly Ser
            130                 135                 140

Asn Ala Gly Lys Gly Glu Ser Leu His His Thr Ala Leu Arg Phe Arg
145                 150                 155                 160

Ile Leu Lys Gln His Gly Tyr Lys Val Ser Gln Glu Val Phe Glu Gly

```
                165                 170                 175
Phe Thr Asp Gln Asn Gly His Phe Lys Ala Cys Leu Cys Lys Asp Val
            180                 185                 190
Lys Gly Met Leu Ser Leu Tyr Glu Ala Ser Tyr Leu Ala Ser Glu Gly
        195                 200                 205
Glu Thr Leu Leu His Glu Ala Met Ala Phe Leu Lys Met His Leu Lys
    210                 215                 220
Asp Leu Glu Gly Thr Leu Asp Lys Ser Leu Glu Glu Leu Val Asn His
225                 230                 235                 240
Ala Met Glu Leu Pro Leu His Arg Arg Met Pro Arg Leu Glu Ala Arg
                245                 250                 255
Trp Phe Ile Glu Ala Tyr Lys Arg Arg Glu Gly Ala Asp Asp Val Leu
            260                 265                 270
Leu Glu Leu Ala Ile Leu Asp Phe Asn Met Val Gln Trp Thr Leu Gln
        275                 280                 285
Asp Asp Leu Gln Asp Met Ser Arg Trp Trp Lys Asp Met Gly Leu Ala
    290                 295                 300
Ser Lys Leu His Phe Ala Arg Asp Arg Leu Met Glu Cys Phe Phe Trp
305                 310                 315                 320
Thr Val Gly Met Ala Phe Glu Pro Glu Phe Ser Asn Cys Arg Lys Gly
                325                 330                 335
Leu Thr Lys Val Thr Ser Phe Ile Thr Ile Asp Asp Val Tyr Asp
            340                 345                 350
Val Tyr Gly Ser Val Asp Glu Leu Glu Leu Phe Thr Asp Ala Val Ala
        355                 360                 365
Arg Trp Asp Ile Asn Met Val Asn Asn Leu Pro Gly Tyr Met Lys Leu
    370                 375                 380
Cys Phe Leu Ala Leu Tyr Asn Thr Val Asn Glu Met Ala Tyr Asp Thr
385                 390                 395                 400
Leu Lys Glu Gln Gly His Asn Ile Leu Pro Tyr Leu Thr Lys Ala Trp
                405                 410                 415
Ala Asp Leu Cys Lys Val Phe Leu Val Glu Ala Lys Trp Cys His Lys
            420                 425                 430
Glu Tyr Thr Pro Thr Phe Glu Glu Tyr Leu Glu Asn Gly Trp Arg Ser
        435                 440                 445
Val Ser Gly Ala Ala Ile Leu Ile His Ala Tyr Phe Leu Met Ser Lys
    450                 455                 460
Asn Ile Thr Lys Glu Ala Leu Glu Cys Leu Glu Asn Asp His Glu Leu
465                 470                 475                 480
Leu Arg Trp Pro Ser Thr Ile Phe Arg Leu Cys Asn Asp Leu Ala Thr
                485                 490                 495
Ser Lys Ala Glu Leu Glu Arg Gly Glu Ser Ala Asn Ser Ile Ser Cys
            500                 505                 510
Tyr Met His Gln Thr Gly Val Ser Glu Asp Ala Arg Glu His Met
        515                 520                 525
Lys Ile Leu Ile Asp Glu Ser Trp Lys Met Asn Lys Val Arg Glu
    530                 535                 540
Met Asp Ser Asp Ser Pro Phe Ala Lys Pro Phe Val Glu Thr Ala Ile
545                 550                 555                 560
Asn Leu Ala Arg Ile Ala Gln Cys Thr Tyr Gln Tyr Gly Asp Ser His
                565                 570                 575
Gly Ala Pro Asp Ala Arg Ser Lys Lys Arg Val Leu Ser Leu Ile Val
            580                 585                 590
```

```
Glu Pro Ile Pro Met Asn Leu Lys Lys
        595                 600
```

<210> SEQ ID NO 3
<211> LENGTH: 576
<212> TYPE: PRT
<213> ORGANISM: Malus domestica

<400> SEQUENCE: 3

```
Met Glu Phe Arg Val His Leu Gln Ala Asp Asn Glu Gln Lys Ile Phe
1               5                   10                  15

Gln Asn Gln Met Lys Pro Glu Pro Glu Ala Ser Tyr Leu Ile Asn Gln
            20                  25                  30

Arg Arg Ser Ala Asn Tyr Lys Pro Asn Ile Trp Lys Asn Asp Phe Leu
        35                  40                  45

Asp Gln Ser Leu Ile Ser Lys Tyr Asp Gly Asp Glu Tyr Arg Lys Leu
    50                  55                  60

Ser Glu Lys Leu Ile Glu Glu Val Lys Ile Tyr Ile Ser Ala Glu Thr
65                  70                  75                  80

Met Asp Leu Val Ala Lys Leu Glu Leu Ile Asp Ser Val Arg Lys Leu
                85                  90                  95

Gly Leu Ala Asn Leu Phe Glu Lys Glu Ile Lys Glu Ala Leu Asp Ser
            100                 105                 110

Ile Ala Ala Ile Glu Ser Asp Asn Leu Gly Thr Arg Asp Asp Leu Tyr
        115                 120                 125

Gly Thr Ala Leu His Phe Lys Ile Leu Arg Gln His Gly Tyr Lys Val
    130                 135                 140

Ser Gln Asp Ile Phe Gly Arg Phe Met Asp Glu Lys Gly Thr Leu Glu
145                 150                 155                 160

Asn His His Phe Ala His Leu Lys Gly Met Leu Glu Leu Phe Glu Ala
                165                 170                 175

Ser Asn Leu Gly Phe Glu Gly Glu Asp Ile Leu Asp Glu Ala Lys Ala
            180                 185                 190

Ser Leu Thr Leu Ala Leu Arg Asp Ser Gly His Ile Cys Tyr Pro Asp
        195                 200                 205

Ser Asn Leu Ser Arg Asp Val Val His Ser Leu Glu Leu Pro Ser His
    210                 215                 220

Arg Arg Val Gln Trp Phe Asp Val Lys Trp Gln Ile Asn Ala Tyr Glu
225                 230                 235                 240

Lys Asp Ile Cys Arg Val Asn Ala Thr Leu Leu Glu Leu Ala Lys Leu
                245                 250                 255

Asn Phe Asn Val Val Gln Ala Gln Leu Gln Lys Asn Leu Arg Glu Ala
            260                 265                 270

Ser Arg Trp Trp Ala Asn Leu Gly Ile Ala Asp Asn Leu Lys Phe Ala
        275                 280                 285

Arg Asp Arg Leu Val Glu Cys Phe Ala Cys Ala Val Gly Val Ala Phe
    290                 295                 300

Glu Pro Glu His Ser Ser Phe Arg Ile Cys Leu Thr Lys Val Ile Asn
305                 310                 315                 320

Leu Val Leu Ile Ile Asp Asp Val Tyr Asp Ile Tyr Gly Ser Glu Glu
                325                 330                 335

Glu Leu Lys His Phe Thr Asn Ala Val Asp Arg Trp Asp Ser Arg Glu
            340                 345                 350

Thr Glu Gln Leu Pro Glu Cys Met Lys Met Cys Phe Gln Val Leu Tyr
```

```
                    355                 360                 365
Asn Thr Thr Cys Glu Ile Ala Arg Glu Ile Glu Glu Asn Gly Trp
370                 375                 380
Asn Gln Val Leu Pro Gln Leu Thr Lys Val Trp Ala Asp Phe Cys Lys
385                 390                 395                 400
Ala Leu Leu Val Glu Ala Glu Trp Tyr Asn Lys Ser His Ile Pro Thr
                405                 410                 415
Leu Glu Glu Tyr Leu Arg Asn Gly Cys Ile Ser Ser Val Ser Val
                420                 425                 430
Leu Leu Val His Ser Phe Phe Ser Ile Thr His Glu Gly Thr Lys Glu
                435                 440                 445
Met Ala Asp Phe Leu His Lys Asn Glu Asp Leu Leu Tyr Asn Ile Ser
450                 455                 460
Leu Ile Val Arg Leu Asn Asn Asp Leu Gly Thr Ser Ala Ala Glu Gln
465                 470                 475                 480
Glu Arg Gly Asp Ser Pro Ser Ser Ile Val Cys Tyr Met Arg Glu Val
                485                 490                 495
Asn Ala Ser Glu Glu Thr Ala Arg Lys Asn Ile Lys Gly Met Ile Asp
                500                 505                 510
Asn Ala Trp Lys Lys Val Asn Gly Lys Cys Phe Thr Thr Asn Gln Val
                515                 520                 525
Pro Phe Leu Ser Ser Phe Met Asn Asn Ala Thr Asn Met Ala Arg Val
                530                 535                 540
Ala His Ser Leu Tyr Lys Asp Gly Asp Gly Phe Gly Asp Gln Glu Lys
545                 550                 555                 560
Gly Pro Arg Thr His Ile Leu Ser Leu Leu Phe Gln Pro Leu Val Asn
                565                 570                 575

<210> SEQ ID NO 4
<211> LENGTH: 583
<212> TYPE: PRT
<213> ORGANISM: Melaleuca alternifolia

<400> SEQUENCE: 4

Met Ala Leu Arg Leu Leu Ser Thr Pro His Leu Pro Gln Leu Cys Ser
1               5                   10                  15
Arg Arg Val Ser Gly Arg Val His Cys Ser Ala Ser Thr Gln Val Ser
                20                  25                  30
Asp Ala Gln Gly Gly Arg Arg Ser Ala Asn Tyr Gln Pro Ser Val Trp
                35                  40                  45
Thr Tyr Asn Tyr Leu Gln Ser Leu Val Ala Asp Ile Arg Arg Ser
50                  55                  60
Arg Arg Glu Val Glu Gln Glu Arg Glu Lys Ala Gln Ile Leu Glu Glu
65                  70                  75                  80
Asp Val Arg Gly Ala Leu Asn Asp Gly Asn Ala Glu Pro Met Ala Ile
                85                  90                  95
Phe Ala Leu Val Asp Asp Ile Gln Arg Leu Gly Leu Gly Arg Tyr Phe
                100                 105                 110
Glu Glu Asp Ile Ser Lys Ala Leu Arg Arg Cys Leu Ser Gln Tyr Ala
                115                 120                 125
Val Thr Gly Ser Leu Gln Lys Ser Leu His Gly Thr Ala Leu Ser Phe
                130                 135                 140
Arg Val Leu Arg Gln His Gly Phe Glu Val Ser Gln Asp Val Phe Lys
145                 150                 155                 160
```

```
Ile Phe Met Asp Glu Ser Gly Ser Phe Met Lys Thr Leu Gly Gly Asp
            165                 170                 175

Val Gln Gly Met Leu Ser Leu Tyr Glu Ala Ser His Leu Ala Phe Glu
        180                 185                 190

Glu Glu Asp Ile Leu His Lys Ala Lys Thr Phe Ala Ile Lys His Leu
        195                 200                 205

Glu Asn Leu Asn His Asp Ile Asp Gln Asp Leu Gln Asp His Val Asn
    210                 215                 220

His Glu Leu Glu Leu Pro Leu His Arg Arg Met Pro Leu Leu Glu Ala
225                 230                 235                 240

Arg Arg Phe Ile Glu Ala Tyr Ser Arg Ser Asn Val Asn Pro Arg
            245                 250                 255

Ile Leu Glu Leu Ala Val Met Lys Phe Asn Ser Ser Gln Leu Thr Leu
            260                 265                 270

Gln Arg Asp Leu Gln Asp Met Leu Gly Trp Trp Asn Val Gly Leu
        275                 280                 285

Ala Lys Arg Leu Ser Phe Ala Arg Asp Arg Leu Met Glu Cys Phe Phe
    290                 295                 300

Trp Ala Val Gly Ile Ala Arg Glu Pro Ala Leu Ser Asn Cys Arg Lys
305                 310                 315                 320

Gly Val Thr Lys Ala Phe Ser Leu Ile Leu Val Leu Asp Asp Val Tyr
            325                 330                 335

Asp Val Phe Gly Thr Leu Asp Glu Leu Glu Leu Phe Thr Asp Ala Val
            340                 345                 350

Arg Arg Trp His Glu Asp Ala Val Glu Asn Leu Pro Gly Tyr Met Lys
        355                 360                 365

Leu Cys Phe Leu Ala Leu Tyr Asn Ser Val Asn Asp Met Ala Tyr Glu
370                 375                 380

Thr Leu Lys Glu Thr Gly Glu Asn Val Thr Pro Tyr Leu Thr Lys Val
385                 390                 395                 400

Trp Tyr Asp Leu Cys Lys Ala Phe Leu Gln Glu Ala Lys Trp Ser Tyr
            405                 410                 415

Asn Lys Ile Thr Pro Gly Val Glu Glu Tyr Leu Asn Asn Gly Trp Val
            420                 425                 430

Ser Ser Ser Gly Gln Val Met Leu Thr His Ala Tyr Phe Leu Ser Ser
        435                 440                 445

Pro Ser Leu Arg Lys Glu Glu Leu Gly Ser Leu Glu His Tyr His Asp
    450                 455                 460

Leu Leu Arg Leu Pro Ser Leu Ile Phe Arg Leu Thr Asn Asp Leu Ala
465                 470                 475                 480

Thr Ser Ser Ala Glu Leu Gly Arg Gly Glu Thr Thr Asn Ser Ile Leu
            485                 490                 495

Cys Tyr Met Arg Glu Lys Gly Phe Ser Glu Ser Glu Ala Arg Lys Gln
            500                 505                 510

Val Ile Glu Gln Ile Asp Thr Ala Trp Arg Gln Met Asn Lys Tyr Met
        515                 520                 525

Val Asp His Ser Thr Phe Asn Arg Ser Phe Met Gln Met Thr Tyr Asn
    530                 535                 540

Leu Ala Arg Met Ala His Cys Val Tyr Gln Asp Gly Asp Ala Ile Gly
545                 550                 555                 560

Ala Pro Asp Asp Gln Ser Trp Asn Arg Val His Ser Leu Ile Ile Lys
            565                 570                 575

Pro Val Ser Leu Ala Pro Cys
```

<210> SEQ ID NO 5
<211> LENGTH: 593
<212> TYPE: PRT
<213> ORGANISM: Phaseolus lunatus

<400> SEQUENCE: 5

```
Met Leu Leu Asn Ser Ser Phe Ile Ser Arg Val Thr Phe Ala Lys Pro
1               5                   10                  15

Leu Lys Pro Val Ala Pro Asn Leu Leu His Arg Arg Ile Ile Phe Pro
            20                  25                  30

Arg Cys Asn Gly Thr Thr Ile Asn Val Asn Ala Ser Glu Arg Lys Ser
        35                  40                  45

Ala Asn Tyr Gln Pro Asn Leu Trp Thr Tyr Asp Phe Leu Gln Ser Leu
    50                  55                  60

Lys His Ala Tyr Ala Asp Thr Arg Tyr Glu Asp Arg Ala Lys Gln Leu
65                  70                  75                  80

Gln Glu Glu Val Arg Lys Met Ile Lys Asp Glu Asn Ser Asp Met Trp
                85                  90                  95

Leu Lys Leu Glu Leu Ile Asn Asp Val Lys Arg Leu Gly Leu Ser Tyr
            100                 105                 110

His Tyr Asp Lys Glu Ile Gly Glu Ala Leu Leu Arg Phe His Ser Ser
        115                 120                 125

Ala Thr Phe Ser Gly Thr Ile Val His Arg Ser Leu His Glu Thr Ala
    130                 135                 140

Leu Cys Phe Arg Leu Leu Arg Glu Tyr Gly Tyr Asp Val Thr Ala Asp
145                 150                 155                 160

Met Phe Glu Arg Phe Lys Glu Arg Asn Gly His Phe Lys Ala Ser Leu
                165                 170                 175

Met Ser Asp Val Lys Gly Met Leu Ser Leu Tyr Gln Ala Ser Phe Leu
            180                 185                 190

Gly Tyr Glu Gly Glu Gln Ile Leu Asp Asp Ala Lys Ala Phe Ser Ser
        195                 200                 205

Phe His Leu Lys Ser Val Leu Ser Glu Gly Arg Asn Asn Met Val Leu
    210                 215                 220

Glu Glu Val Asn His Ala Leu Glu Leu Pro Leu His His Arg Ile Gln
225                 230                 235                 240

Arg Leu Glu Ala Arg Trp Tyr Ile Glu Tyr Tyr Ala Lys Gln Arg Asp
                245                 250                 255

Ser Asn Arg Val Leu Leu Glu Ala Ala Lys Leu Asp Phe Asn Ile Leu
            260                 265                 270

Gln Ser Thr Leu Gln Asn Asp Leu Gln Glu Val Ser Arg Trp Trp Lys
        275                 280                 285

Gly Met Gly Leu Ala Ser Lys Leu Ser Phe Ser Arg Asp Arg Leu Met
    290                 295                 300

Glu Cys Phe Phe Trp Ala Ala Gly Met Val Phe Glu Pro Gln Phe Ser
305                 310                 315                 320

Asp Leu Arg Lys Gly Leu Thr Lys Val Ala Ser Leu Ile Thr Thr Ile
                325                 330                 335

Asp Asp Val Tyr Asp Val Tyr Gly Thr Leu Glu Glu Leu Glu Leu Phe
            340                 345                 350

Thr Ala Ala Val Glu Ser Trp Asp Val Lys Ala Ile Gln Val Leu Pro
        355                 360                 365
```

```
Asp Tyr Met Lys Ile Cys Phe Leu Ala Leu Tyr Asn Thr Val Asn Glu
    370                 375                 380

Phe Ala Tyr Asp Ala Leu Lys Glu Gln Gly Gln Asp Ile Leu Pro Tyr
385                 390                 395                 400

Leu Thr Lys Ala Trp Ser Asp Leu Leu Lys Ala Phe Leu Gln Glu Ala
                405                 410                 415

Lys Trp Ser Arg Asp Arg His Met Pro Arg Phe Asn Asp Tyr Leu Asn
            420                 425                 430

Asn Ala Trp Val Ser Val Ser Gly Val Val Leu Leu Thr His Ala Tyr
        435                 440                 445

Phe Leu Leu Asn His Ser Ile Thr Glu Glu Ala Leu Glu Ser Leu Asp
    450                 455                 460

Ser Tyr His Ser Leu Leu Gln Asn Thr Ser Leu Val Phe Arg Leu Cys
465                 470                 475                 480

Asn Asp Leu Gly Thr Ser Lys Ala Glu Leu Glu Arg Gly Glu Ala Ala
                485                 490                 495

Ser Ser Ile Leu Cys Tyr Arg Arg Glu Ser Gly Ala Ser Glu Glu Gly
            500                 505                 510

Ala Tyr Lys His Ile Tyr Ser Leu Leu Asn Glu Thr Trp Lys Lys Met
        515                 520                 525

Asn Glu Asp Arg Val Ser Gln Ser Pro Phe Pro Lys Ala Phe Val Glu
    530                 535                 540

Thr Ala Met Asn Leu Ala Arg Ile Ser His Cys Thr Tyr Gln Tyr Gly
545                 550                 555                 560

Asp Gly His Gly Ala Pro Asp Ser Thr Ala Lys Asn Arg Ile Arg Ser
                565                 570                 575

Leu Ile Ile Glu Pro Ile Ala Leu Tyr Glu Thr Glu Ile Ser Thr Ser
            580                 585                 590

Tyr

<210> SEQ ID NO 6
<211> LENGTH: 628
<212> TYPE: PRT
<213> ORGANISM: Abies grandis

<400> SEQUENCE: 6

Met Ala Leu Val Ser Thr Ala Pro Leu Ala Ser Lys Ser Cys Leu His
1               5                   10                  15

Lys Ser Leu Ile Ser Ser Thr His Glu Leu Lys Ala Leu Ser Arg Thr
            20                  25                  30

Ile Pro Ala Leu Gly Met Ser Arg Arg Gly Lys Ser Ile Thr Pro Ser
        35                  40                  45

Ile Ser Met Ser Ser Thr Thr Val Val Thr Asp Asp Gly Val Arg Arg
    50                  55                  60

Arg Met Gly Asp Phe His Ser Asn Leu Trp Asp Asp Asp Val Ile Gln
65                  70                  75                  80

Ser Leu Pro Thr Ala Tyr Glu Glu Lys Ser Tyr Leu Glu Arg Ala Glu
                85                  90                  95

Lys Leu Ile Gly Glu Val Lys Asn Met Phe Asn Ser Met Ser Leu Glu
            100                 105                 110

Asp Gly Glu Leu Met Ser Pro Leu Asn Asp Leu Ile Gln Arg Leu Trp
        115                 120                 125

Ile Val Asp Ser Leu Glu Arg Leu Gly Ile His Arg His Phe Lys Asp
    130                 135                 140
```

-continued

```
Glu Ile Lys Ser Ala Leu Asp Tyr Val Tyr Ser Tyr Trp Gly Glu Asn
145                 150                 155                 160

Gly Ile Gly Cys Gly Arg Glu Ser Val Val Thr Asp Leu Asn Ser Thr
                165                 170                 175

Ala Leu Gly Leu Arg Thr Leu Arg Leu His Gly Tyr Pro Val Ser Ser
            180                 185                 190

Asp Val Phe Lys Ala Phe Lys Gly Gln Asn Gly Gln Phe Ser Cys Ser
        195                 200                 205

Glu Asn Ile Gln Thr Asp Glu Ile Arg Gly Val Leu Asn Leu Phe
    210                 215                 220

Arg Ala Ser Leu Ile Ala Phe Pro Gly Glu Lys Ile Met Asp Glu Ala
225                 230                 235                 240

Glu Ile Phe Ser Thr Lys Tyr Leu Lys Glu Ala Leu Gln Lys Ile Pro
                245                 250                 255

Val Ser Ser Leu Ser Arg Glu Ile Gly Asp Val Leu Glu Tyr Gly Trp
            260                 265                 270

His Thr Tyr Leu Pro Arg Leu Glu Ala Arg Asn Tyr Ile Gln Val Phe
        275                 280                 285

Gly Gln Asp Thr Glu Asn Thr Lys Ser Tyr Val Lys Ser Lys Lys Leu
    290                 295                 300

Leu Glu Leu Ala Lys Leu Glu Phe Asn Ile Phe Gln Ser Leu Gln Lys
305                 310                 315                 320

Arg Glu Leu Glu Ser Leu Val Arg Trp Trp Lys Glu Ser Gly Phe Pro
                325                 330                 335

Glu Met Thr Phe Cys Arg His Arg His Val Glu Tyr Tyr Thr Leu Ala
            340                 345                 350

Ser Cys Ile Ala Phe Glu Pro Gln His Ser Gly Phe Arg Leu Gly Phe
        355                 360                 365

Ala Lys Thr Cys His Leu Ile Thr Val Leu Asp Asp Met Tyr Asp Thr
    370                 375                 380

Phe Gly Thr Val Asp Glu Leu Glu Leu Phe Thr Ala Thr Met Lys Arg
385                 390                 395                 400

Trp Asp Pro Ser Ser Ile Asp Cys Leu Pro Glu Tyr Met Lys Gly Val
                405                 410                 415

Tyr Ile Ala Val Tyr Asp Thr Val Asn Glu Met Ala Arg Glu Ala Glu
            420                 425                 430

Glu Ala Gln Gly Arg Asp Thr Leu Thr Tyr Ala Arg Glu Ala Trp Glu
        435                 440                 445

Ala Tyr Ile Asp Ser Tyr Met Gln Glu Ala Arg Trp Ile Ala Thr Gly
    450                 455                 460

Tyr Leu Pro Ser Phe Asp Glu Tyr Tyr Glu Asn Gly Lys Val Ser Cys
465                 470                 475                 480

Gly His Arg Ile Ser Ala Leu Gln Pro Ile Leu Thr Met Asp Ile Pro
                485                 490                 495

Phe Pro Asp His Ile Leu Lys Glu Val Asp Phe Pro Ser Lys Leu Asn
            500                 505                 510

Asp Leu Ala Cys Ala Ile Leu Arg Leu Arg Gly Asp Thr Arg Cys Tyr
        515                 520                 525

Lys Ala Asp Arg Ala Arg Gly Glu Glu Ala Ser Ser Ile Ser Cys Tyr
    530                 535                 540

Met Lys Asp Asn Pro Gly Val Ser Glu Glu Asp Ala Leu Asp His Ile
545                 550                 555                 560

Asn Ala Met Ile Ser Asp Val Ile Lys Gly Leu Asn Trp Glu Leu Leu
```

```
            565                 570                 575
Lys Pro Asp Ile Asn Val Pro Ile Ser Ala Lys Lys His Ala Phe Asp
            580                 585                 590

Ile Ala Arg Ala Phe His Tyr Gly Tyr Lys Tyr Arg Asp Gly Tyr Ser
            595                 600                 605

Val Ala Asn Val Glu Thr Lys Ser Leu Val Thr Arg Thr Leu Leu Glu
            610                 615                 620

Ser Val Pro Leu
625

<210> SEQ ID NO 7
<211> LENGTH: 337
<212> TYPE: PRT
<213> ORGANISM: Streptomyces sp.

<400> SEQUENCE: 7

Met Pro Gln Asp Val Asp Phe His Ile Pro Leu Pro Gly Arg Gln Ser
1               5                   10                  15

Pro Asp His Ala Arg Ala Glu Ala Glu Gln Leu Ala Trp Pro Arg Ser
                20                  25                  30

Leu Gly Leu Ile Arg Ser Asp Ala Ala Ala Glu Arg His Leu Arg Gly
            35                  40                  45

Gly Tyr Ala Asp Leu Ala Ser Arg Phe Tyr Pro His Ala Thr Gly Ala
        50                  55                  60

Asp Leu Asp Leu Gly Val Asp Leu Met Ser Trp Phe Phe Leu Phe Asp
65                  70                  75                  80

Asp Leu Phe Asp Gly Pro Arg Gly Glu Asn Pro Glu Thr Lys Gln
                85                  90                  95

Leu Thr Asp Gln Val Ala Ala Leu Asp Gly Pro Leu Pro Asp Thr
            100                 105                 110

Ala Pro Pro Ile Ala His Gly Phe Ala Asp Ile Trp Arg Arg Thr Cys
            115                 120                 125

Glu Gly Met Thr Pro Ala Trp Cys Ala Arg Ser Ala Arg His Trp Arg
130                 135                 140

Asn Tyr Phe Asp Gly Tyr Val Asp Glu Ala Glu Ser Arg Phe Trp Asn
145                 150                 155                 160

Ala Pro Cys Asp Ser Ala Ala Gln Tyr Leu Ala Met Arg Arg His Thr
                165                 170                 175

Ile Gly Val Gln Pro Thr Val Asp Leu Ala Glu Arg Ala Gly Arg Phe
            180                 185                 190

Glu Val Pro His Arg Val Phe Asp Ser Ala Val Met Ser Ala Met Leu
        195                 200                 205

Gln Ile Ala Val Asp Val Asn Leu Leu Leu Asn Asp Ile Ala Ser Leu
    210                 215                 220

Glu Lys Glu Glu Ala Arg Gly Glu Gln Asn Asn Met Val Met Ile Leu
225                 230                 235                 240

Arg Arg Glu His Gly Trp Ser Lys Ser Arg Ser Val Ser His Met Gln
                245                 250                 255

Asn Glu Val Arg Ala Arg Leu Gly Gln Tyr Leu Leu Leu Glu Ser Cys
            260                 265                 270

Leu Pro Lys Val Gly Glu Ile Tyr Gln Leu Asp Thr Ala Glu Arg Glu
        275                 280                 285

Ala Leu Glu Arg Tyr Arg Thr Asp Ala Val Arg Thr Val Ile Arg Gly
    290                 295                 300
```

```
Ser Tyr Asp Trp His Arg Ser Gly Arg Tyr Asp Ala Glu Phe Ala
305                 310                 315                 320

Leu Ala Ala Gly Ala Gln Gly Tyr Leu Glu Glu Leu Gly Ser Ser Ala
                325                 330                 335

His

<210> SEQ ID NO 8
<211> LENGTH: 546
<212> TYPE: PRT
<213> ORGANISM: Ocimum basilicum

<400> SEQUENCE: 8

Met Thr Asn Met Phe Ala Ser Ala Ala Pro Ile Ser Thr Asn Asn Thr
1               5                   10                  15

Thr Val Glu Asp Met Arg Arg Ser Val Thr Tyr His Pro Ser Val Trp
            20                  25                  30

Lys Asp His Phe Leu Asp Tyr Ala Ser Gly Ile Thr Glu Val Glu Met
        35                  40                  45

Glu Gln Leu Gln Lys Gln Lys Glu Arg Ile Lys Thr Leu Leu Ala Gln
    50                  55                  60

Thr Leu Asp Asp Phe Val Leu Lys Ile Glu Leu Ile Asp Ala Ile Gln
65                  70                  75                  80

Arg Leu Gly Val Gly Tyr His Phe Glu Lys Glu Ile Asn His Ser Leu
                85                  90                  95

Arg Gln Ile Tyr Asp Thr Phe Gln Ile Ser Ser Lys Asp Asn Asp Ile
            100                 105                 110

Arg Val Val Ala Leu Arg Phe Arg Leu Leu Arg Gln His Gly Tyr Pro
        115                 120                 125

Val Pro Ser Asp Val Phe Lys Lys Phe Ile Asp Asn Gln Gly Arg Leu
    130                 135                 140

Asp Glu Ser Val Met Asn Asn Val Glu Gly Met Leu Ser Leu Tyr Glu
145                 150                 155                 160

Ala Ser Asn Tyr Gly Met Glu Gly Glu Asp Ile Leu Asp Lys Ala Leu
                165                 170                 175

Glu Ile Ser Thr Ser His Leu Glu Pro Leu Ala Ser Arg Ser Arg Arg
            180                 185                 190

Ile Asn Glu Ala Leu Glu Met Pro Ile Ser Lys Thr Leu Val Arg Leu
        195                 200                 205

Gly Ala Arg Lys Phe Ile Ser Ile Tyr Glu Glu Asp Glu Ser Arg Asp
    210                 215                 220

Glu Asp Leu Leu Lys Phe Ala Lys Leu Asp Phe Asn Ile Leu Gln Lys
225                 230                 235                 240

Ile His Gln Glu Glu Leu Thr His Ile Ala Arg Trp Trp Lys Glu Leu
                245                 250                 255

Asp Leu Gly Asn Lys Leu Pro Phe Ala Arg Asp Arg Val Val Glu Cys
            260                 265                 270

Tyr Phe Trp Ile Leu Gly Val Tyr Phe Glu Pro Gln Tyr Asn Ile Ala
        275                 280                 285

Arg Arg Phe Met Thr Lys Val Ile Ala Met Thr Ser Ile Ile Asp Asp
    290                 295                 300

Ile Tyr Asp Val His Gly Thr Leu Glu Glu Leu Gln Arg Phe Thr Asp
305                 310                 315                 320

Ala Ile Arg Ser Trp Asp Ile Arg Ala Ile Asp Glu Leu Pro Pro Tyr
                325                 330                 335
```

```
Met Arg Leu Cys Tyr Glu Ala Leu Leu Gly Met Tyr Ala Glu Met Glu
            340                 345                 350

Asn Glu Met Val Lys Gln Asn Gln Ser Tyr Arg Ile Glu Tyr Ala Arg
        355                 360                 365

Gln Glu Met Ile Lys Leu Val Thr Thr Tyr Met Glu Glu Ala Lys Trp
    370                 375                 380

Cys Tyr Ser Lys Tyr Ile Pro Asn Met Asp Glu Tyr Met Lys Leu Ala
385                 390                 395                 400

Leu Val Ser Gly Ala Tyr Met Met Leu Ala Thr Thr Ser Leu Val Gly
                405                 410                 415

Ile Leu Gly Asp Pro Ile Thr Lys Gln Asp Phe Asp Trp Ile Thr Asn
            420                 425                 430

Glu Pro Pro Ile Leu Arg Ala Ala Ser Val Ile Cys Arg Leu Met Asp
        435                 440                 445

Asp Val Val Gly His Gly Ile Glu Gln Lys Ile Ser Ser Val Asp Cys
    450                 455                 460

Tyr Met Lys Glu Asn Gly Cys Ser Lys Met Glu Ala Val Gly Glu Phe
465                 470                 475                 480

Ser Lys Arg Val Lys Lys Ala Trp Lys Asn Leu Asn Glu Glu Trp Val
                485                 490                 495

Glu Pro Arg Ala Ala Ser Met Val Ile Leu Val Arg Val Val Asn Leu
            500                 505                 510

Ala Arg Val Ile Asn Leu Leu Tyr Val Gly Glu Asp Ser Tyr Gly Asn
        515                 520                 525

Ser Ser Val Lys Thr Lys Glu Leu Ile Lys Gly Val Leu Val His Pro
    530                 535                 540

Ile Lys
545

<210> SEQ ID NO 9
<211> LENGTH: 554
<212> TYPE: PRT
<213> ORGANISM: Zingiber zerumbet

<400> SEQUENCE: 9

Met Glu Lys Gln Ser Leu Thr Phe Asp Gly Asp Glu Glu Ala Lys Ile
1               5                   10                  15

Asp Arg Lys Ser Ser Lys Tyr His Pro Ser Ile Trp Gly Asp Tyr Phe
            20                  25                  30

Ile Gln Asn Ser Ser Leu Thr His Ala Lys Glu Ser Thr Gln Arg Met
        35                  40                  45

Ile Lys Arg Val Glu Glu Leu Lys Val Gln Val Lys Ser Met Phe Lys
    50                  55                  60

Asp Thr Ser Asp Leu Leu Gln Leu Met Asn Leu Ile Asn Ser Ile Gln
65                  70                  75                  80

Met Leu Gly Leu Asp Tyr His Phe Glu Asn Glu Ile Asp Glu Ala Leu
                85                  90                  95

Arg Leu Ile Tyr Glu Val Asp Asp Lys Ser Tyr Gly Leu Tyr Glu Thr
            100                 105                 110

Ser Leu Arg Phe Gln Leu Leu Arg Gln His Gly Tyr His Val Ser Ala
        115                 120                 125

Asp Ile Phe Asn Lys Phe Lys Asp Asp Asn Gly Ser Phe Ile Ser Ser
    130                 135                 140

Leu Asn Gly Asp Ala Lys Gly Leu Leu Ser Leu Tyr Asn Val Ser Tyr
145                 150                 155                 160
```

Leu Gly Thr His Gly Glu Thr Ile Leu Asp Glu Ala Lys Ser Phe Thr
            165                 170                 175

Lys Pro Gln Leu Val Ser Leu Met Ser Glu Leu Glu Gln Ser Leu Ala
        180                 185                 190

Ala Gln Val Ser Leu Phe Leu Glu Leu Pro Leu Cys Arg Arg Asn Lys
    195                 200                 205

Ile Leu Leu Ala Arg Lys Tyr Ile Leu Ile Tyr Gln Glu Asp Ala Met
210                 215                 220

Arg Asn Asn Val Ile Leu Glu Leu Ala Lys Leu Asn Phe Asn Leu Leu
225                 230                 235                 240

Gln Ser Leu Tyr Gln Glu Leu Lys Lys Ile Ser Ile Trp Trp Asn
                245                 250                 255

Asp Leu Ala Phe Ala Lys Ser Leu Ser Phe Thr Arg Asp Arg Val Val
                260                 265                 270

Glu Gly Tyr Tyr Trp Val Leu Thr Ile Tyr Phe Glu Pro Gln His Ser
            275                 280                 285

Arg Ala Arg Val Ile Cys Ser Lys Val Phe Ala Phe Leu Ser Ile Met
        290                 295                 300

Asp Asp Ile Tyr Asp Asn Tyr Gly Ile Leu Glu Glu Cys Thr Leu Leu
305                 310                 315                 320

Thr Glu Ala Ile Lys Arg Trp Asn Pro Gln Ala Ile Asp Gly Leu Pro
                325                 330                 335

Glu Tyr Leu Lys Asp Tyr Tyr Leu Lys Leu Leu Lys Thr Phe Glu Glu
            340                 345                 350

Phe Glu Asp Glu Leu Glu Leu Asn Glu Lys Tyr Arg Met Leu Tyr Leu
        355                 360                 365

Gln Asp Glu Val Lys Ala Leu Ala Ile Ser Tyr Leu Gln Glu Ala Lys
    370                 375                 380

Trp Gly Ile Glu Arg His Val Pro Ser Leu Asp Glu His Leu His Asn
385                 390                 395                 400

Ser Leu Ile Ser Ser Gly Ser Ser Thr Val Ile Cys Ala Ser Phe Val
                405                 410                 415

Gly Met Gly Glu Val Ala Thr Lys Glu Val Phe Asp Trp Leu Ser Ser
            420                 425                 430

Phe Pro Lys Val Val Glu Ala Cys Cys Val Ile Gly Arg Leu Leu Asn
        435                 440                 445

Asp Ile Arg Ser His Glu Leu Glu Gln Gly Arg Asp His Thr Ala Ser
    450                 455                 460

Thr Val Glu Ser Tyr Met Lys Glu His Asp Thr Asn Val Asp Val Ala
465                 470                 475                 480

Cys Glu Lys Leu Arg Glu Ile Val Glu Lys Ala Trp Lys Asp Leu Asn
                485                 490                 495

Asn Glu Ser Leu Asn Pro Thr Lys Val Pro Arg Leu Met Ile Glu Arg
            500                 505                 510

Ile Val Asn Leu Ser Lys Ser Asn Glu Glu Ile Tyr Lys Tyr Asn Asp
        515                 520                 525

Thr Tyr Thr Asn Ser Asp Thr Thr Met Lys Asp Asn Ile Ser Leu Val
    530                 535                 540

Leu Val Glu Ser Cys Asp Tyr Phe Asn Lys
545                 550

<210> SEQ ID NO 10
<211> LENGTH: 631

```
<212> TYPE: PRT
<213> ORGANISM: Alicyclobacillus acidocaldarius subsp. acidocaldarius

<400> SEQUENCE: 10

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Met Glu Lys Ile
    50                  55                  60

Arg Arg Tyr Leu Leu His Glu Gln Arg Glu Asp Gly Thr Trp Ala Leu
65              70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
            115                 120                 125

Phe Thr Arg Met Trp Leu Ala Leu Val Gly Glu Tyr Pro Trp Glu Lys
130             135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
            195                 200                 205

Gly Ala Lys Gly Gly Gly Gly Trp Ile Phe Asp Ala Leu Asp Arg Ala
        210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350
```

```
Val Lys Arg Pro Asn Leu Lys Pro Gly Gly Phe Ala Phe Gln Phe Asp
        355                 360                 365
Asn Val Tyr Tyr Pro Asp Val Asp Asp Thr Ala Val Val Val Trp Ala
        370                 375                 380
Leu Asn Thr Leu Arg Leu Pro Asp Glu Arg Arg Arg Arg Asp Ala Met
385                 390                 395                 400
Thr Lys Gly Phe Arg Trp Ile Val Gly Met Gln Ser Ser Asn Gly Gly
                405                 410                 415
Trp Gly Ala Tyr Asp Val Asp Asn Thr Ser Asp Leu Pro Asn His Ile
                420                 425                 430
Pro Phe Cys Asp Phe Gly Glu Val Thr Asp Pro Pro Ser Glu Asp Val
            435                 440                 445
Thr Ala His Val Leu Glu Cys Phe Gly Ser Phe Gly Tyr Asp Asp Ala
        450                 455                 460
Trp Lys Val Ile Arg Arg Ala Val Glu Tyr Leu Lys Arg Glu Gln Lys
465                 470                 475                 480
Pro Asp Gly Ser Trp Phe Gly Arg Trp Gly Val Asn Tyr Leu Tyr Gly
                485                 490                 495
Thr Gly Ala Val Val Ser Ala Leu Lys Ala Val Gly Ile Asp Thr Arg
            500                 505                 510
Glu Pro Tyr Ile Gln Lys Ala Leu Asp Trp Val Glu Gln His Gln Asn
        515                 520                 525
Pro Asp Gly Gly Trp Gly Glu Asp Cys Arg Ser Tyr Glu Asp Pro Ala
        530                 535                 540
Tyr Ala Gly Lys Gly Ala Ser Thr Pro Ser Gln Thr Ala Trp Ala Leu
545                 550                 555                 560
Met Ala Leu Ile Ala Gly Gly Arg Ala Glu Ser Glu Ala Ala Arg Arg
                565                 570                 575
Gly Val Gln Tyr Leu Val Glu Thr Gln Arg Pro Asp Gly Gly Trp Asp
            580                 585                 590
Glu Pro Tyr Tyr Thr Gly Thr Gly Phe Pro Gly Asp Phe Tyr Leu Gly
            595                 600                 605
Tyr Thr Met Tyr Arg His Val Phe Pro Thr Leu Ala Leu Gly Arg Tyr
    610                 615                 620
Lys Gln Ala Ile Glu Arg Arg
625                 630
```

METHOD FOR PRODUCING A MONOALKENE BY ENZYMATIC CONVERSION OF AN ALKYL MONOESTER

The present invention relates to a method for producing a monoalkene comprising the step of enzymatically converting an alkyl monoester. The conversion preferably makes use of an enzyme which belongs to the family of terpene synthases or to the family of prenyltransferases. Moreover, the present invention relates to the use of a terpene synthase or a prenyltransferase for enzymatically converting an alkyl monoester into a monoalkene.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels. Ethylene, the simplest alkene, lies at the heart of industrial organic chemistry: it is the most widely produced organic compound in the world. It is used in particular to produce polyethylene, a major plastic. Ethylene can also be converted to many industrially useful products by reaction (e.g. by oxidation or halogenation). Propylene plays a similarly important role: its polymerization results in a plastic material, polypropylene. The technical properties of this product in terms of resistance, density, solidity, deformability, and transparency are unequalled. The worldwide market for polypropylene has grown continuously since its invention in 1954. Butylene exists in four forms, one of which, isobutylene, enters into the composition of methyl-tert-butyl-ether (MTBE), an anti-knock additive for automobile fuel. Isobutylene can also be used to produce isooctene, which in turn can be reduced to isooctane (2,2,4-trimethylpentane); the very high octane rating of isooctane makes it the best fuel for so-called "gasoline" engines. Amylene, hexene and heptene exist in many forms according to the position and configuration of the double bond. These products have real industrial applications but are less important than ethylene, propylene or butenes. All these alkenes are currently produced by catalytic cracking of petroleum products (or by a derivative of the Fischer-Tropsch process in the case of hexene, from coal or gas). Their production costs are therefore tightly linked to the price of oil. Moreover, catalytic cracking is sometimes associated with considerable technical difficulties which increase process complexity and production costs.

The production by a biological pathway of alkenes or other organic molecules that can be used as fuels or as precursors of synthetic resins is called for in the context of a sustainable industrial operation in harmony with geochemical cycles. The first generation of biofuels consisted in the fermentative production of ethanol, as fermentation and distillation processes already existed in the food processing industry. The production of second generation biofuels is in an exploratory phase, encompassing in particular the production of long chain alcohols (butanol and pentanol), terpenes, linear alkanes and fatty acids. Two recent reviews provide a general overview of research in this field: Ladygina et al. (Process Biochemistry 41 (2006), 1001) and Wackett (Current Opinions in Chemical Biology 21 (2008), 187).

The production of ethylene by plants has long been known (Meigh et al. (Nature 186 (1960), 902)). According to the metabolic pathway elucidated, methionine is the precursor of ethylene (Adams and Yang (PNAS 76 (1979), 170)). Conversion of 2-oxoglutarate has also been described (Ladygina et al. (Process Biochemistry 41 (2006), 1001). Since a single ethylene molecule requires the previous production of a four- or five-carbon chain, the equipment and energy needs of all these pathways are unfavorable and do not bode well for their industrial application for alkene bioproduction.

Moreover, many microorganisms are capable of producing propylene, however, with an extremely low yield The conversion of isovalerate to isobutylene by the yeast *Rhodotorula minuta* has been described (Fujii et al. (Appl. Environ. Microbiol. 54 (1988), 583)), but the efficiency of this reaction, less than 1 millionth per minute, or about 1 for 1000 per day, is far from permitting an industrial application. The reaction mechanism was elucidated by Fukuda et al. (BBRC 201 (1994), 516) and involves a cytochrome P450 enzyme which decarboxylates isovalerate by reduction of an oxoferryl group $Fe^V=0$. Large-scale biosynthesis of isobutylene by this pathway seems highly unfavorable, since it would require the synthesis and degradation of one molecule of leucine to form one molecule of isobutylene. Also, the enzyme catalyzing the reaction uses heme as cofactor, poorly lending itself to recombinant expression in bacteria and to improvement of enzyme parameters. For all these reasons, it appears very unlikely that this pathway can serve as a basis for industrial exploitation. Other microorganisms have been described as being marginally capable of naturally producing isobutylene from isovalerate; the yields obtained are even lower than those obtained with *Rhodotorula minuta* (Fukuda et al. (Agric. Biol. Chem. 48 (1984), 1679)).

Isoprene is produced at a significant level in higher plants, such as poplars. The production of isoprene in this context remains however low and the pathway which leads to isoprene production, which is based on the mevalonate-isopentenyl-pyrophosphate pathway, poorly complies with the demands for industrial scale production.

Thus, there is still a need for efficient and environmentally friendly methods of producing alkenes, in particular monoalkenes.

The present invention meets this demand by providing a method for producing a monoalkene from an alkyl monoester by employing an enzymatic reaction. More specifically, the present invention relates to a method for producing a monoalkene, the method comprising a step of converting an alkyl monoester into a monoalkene, wherein: the alkyl monoester is a compound of formula (I)

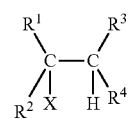

(I)

wherein $R^1$, $R^2$, $R^3$ and $R^4$ are each independently selected from hydrogen (—H), methyl (—CH3) or ethyl (—C2H5); and wherein X is selected from:
  O—PO$_3$H$_2$ monophosphate
  O—PO$_2$H—O—PO$_3$H$_2$ diphosphate
  O—SO$_3$H sulfate
and wherein
the monoalkene is a compound of formula (II)

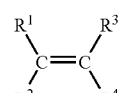

(II)

wherein $R^1$, $R^2$, $R^3$ and $R^4$ have the same meanings as defined for the compound of formula (I),
the method being characterized in that the conversion from the alkyl monoester into the monoalkene is achieved by enzymatic elimination of molecule XH.

The present invention teaches for the first time that it is possible to enzymatically convert an alkyl monoester having formula (I) as shown above into a corresponding monoalkene by eliminating the phosphorus or sulphur containing molecule XH with the help of an enzyme.

In particular, it has been found that enzymes which belong to the family of terpene synthases or to the family of prenyl transferases are capable of catalyzing the conversion of an alkyl monoester into a monoalkene as described above.

The conversion of an alkyl monoester according to formula (I) into a monoalkene according to formula (II) by elimination of molecule XH can in principle be achieved by any enzyme which is capable of eliminating the phosphorus or sulphur containing molecule XH from an alkyl monoester of the formula (I). Preferably, such an enzyme is an enzyme which can be classified as belonging to the terpene synthase family, more preferably the terpene synthase is a plant terpene synthase. In another preferred embodiment such an enzyme is an enzyme which can be classified as belonging to the prenyltransferase family.

The terpene synthases constitute an enzyme family which comprises enzymes catalyzing the formation of numerous natural products always composed of carbon and hydrogen (terpenes) and sometimes also of oxygen or other elements (terpenoids). Terpenoids are structurally diverse and widely distributed molecules corresponding to well over 30000 defined natural compounds that have been identified from all kingdoms of life. In plants, the members of the terpene synthase family are responsible for the synthesis of the various terpene molecules from two isomeric 5-carbon precursor "building blocks", isoprenyl diphosphate and prenyl diphosphate, leading to 5-carbon isoprene, 10-carbon monoterpene, 15-carbon sesquiterpene and 20-carbon diterpenes" (Chen et al.; The Plant Journal 66 (2011), 212-229).

The ability of terpene synthases to convert a prenyl diphosphate containing substrate to diverse products during different reaction cycles is one of the most unique traits of this enzyme class. The common key step for the biosynthesis of all terpenes is the reaction of terpene synthase on corresponding diphosphate esters. The general mechanism of this enzyme class induces the removal of the diphosphate group and the generation of an intermediate with carbocation as the first step. In the various terpene synthases, such intermediates further rearrange to generate the high number of terpene skeletons observed in nature. In particular, the resulting cationic intermediate undergoes a series of cyclizations, hydride shifts or other rearrangements until the reaction is terminated by proton loss or the addition of a nucleophile, in particular water for forming terpenoid alcohols (Degenhardt et al., Phytochemistry 70 (2009), 1621-1637).

The different terpene synthases share various structural features. These include a highly conserved C-terminal domain, which contains their catalytic site and an aspartate-rich DDXXD motif essential for the divalent metal ion (typically Mg2+ or Mn2+) assisted substrate binding in these enzymes (Green et al. Journal of biological chemistry, 284, 13, 8661-8669). In principle, any known enzyme which can be classified as belonging to the EC 4.2.3 enzyme superfamily can be employed.

Even more preferably the method according to the invention makes use of an isoprene synthase (EC 4.2.3.27), a myrcene/ocimene synthase (EC 4.2.3.15), a farnesene synthase (EC 4.2.3.46 or EC 4.2.3.47) or a pinene synthase (EC 4.2.3.14). Also enzymes which are generally classified as monoterpene synthases can be used.

Isoprene synthase (EC 4.2.3.27) is an enzyme which naturally catalyzes the following reaction:

Dimethylallyl diphosphate ⟹ isoprene+diphosphate

This enzyme occurs in a number of organisms, in particular in plants and some bacteria. The occurrence of this enzyme has, e.g., been described for *Arabidopsis thaliana*, a number of *Populus* species like *P. alba* (UniProt accession numbers Q50L36, A9Q7C9, D8UY75 and D8UY76), *P. nigra* (UniProt accession number AOPFK2), *P. canescence* (UniProt accession number Q9AR86; see also Köksal et al., J. Mol. Biol. 402 (2010), 363-373), *P. tremuloides, P. trichocarpa*, in *Quercus petraea, Quercus robur, Salix discolour, Pueraria montana* (UniProt accession number Q6EJ97), *Pueraria lobata, Mucuna pruriens, Vitis vinifera, Embryophyta* and *Bacillus subtilis*. In principle, any known isoprene synthase can be employed in the method according to the invention. In a preferred embodiment, the isoprene synthase employed in a method according to the present invention is an isoprene synthase from a plant of the genus *Populus*, more preferably from *Populus trichocarpa* or *Populus alba*. In another preferred embodiment the isoprene synthase employed in a method according to the present invention is an isoprene synthase from *Pueraria montana*, preferably from *Pueraria Montana* var. *lobata*, or from *Vitis vinifera*. Preferred isoprene synthases to be used in the context of the present invention are the isoprene synthase of *Populus alba* (Sasaki et al.; FEBS Letters 579 (2005), 2514-2518) or the isoprene synthases from *Populus trichocarpa* and *Populus tremuloides* which show very high sequence homology to the isoprene synthase from *Populus alba*. Another preferred isoprene synthase is the isoprene synthase from *Pueraria montana* var. *lobata* (kudzu) (Sharkey et al.; Plant Physiol. 137 (2005), 700-712). The activity of an isoprene synthase can be measured according to methods known in the art, e.g. as described in Silver and Fall (Plant Physiol (1991) 97, 1588-1591). In a typical assay, the enzyme is incubated with dimethylallyl diphosphate in the presence of the required co-factors, $Mg^{2+}$ or $Mn^{2+}$ and $K^+$ in sealed vials. At appropriate time volatiles compound in the headspace are collected with a gas-tight syringe and analyzed for isoprene production by gas chromatography (GC).

Myrcene/ocimene synthases (EC 4.2.3.15) are enzymes which naturally catalyze the following reaction:

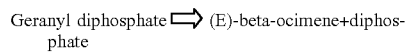
Geranyl diphosphate ⟹ (E)-beta-ocimene+diphosphate or

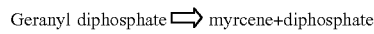
Geranyl diphosphate ⟹ myrcene+diphosphate

These enzymes occur in a number of organisms, in particular in plants and animals, for example in *Lotus japanicus, Phaseolus lunatus, Abies grandis, Arabidopsis thaliana* (UniProt accession number Q9ZUH4), *Actinidia chinensis, Perilla fructescens, Ochtodes secundiramea* and in *Ips pini* (UniProt accession number Q58GE8. In principle, any known myrcene/ocimene synthase can be employed in the method according to the invention. In a preferred embodiment, the myrcene/ocimene synthase employed in a method according to the present invention is a myrcene/ocimene synthase from *Lotus japanicus* (Arimura et al.; Plant Physiol. 135 (2004), 1976-1983) or from *Phaseolus lunatus* (UniProt accession number B1P189). The activity of an ocimene/myrcene synthase can be measured as described, for example, in Arimura et al. (Plant Physiology 135 (2004), 1976-1983. In a typical assay for determining the activity, the enzyme is placed in screwcapped glass test tube containing divalent metal ions, e.g. $Mg^{2+}$ and/or $Mn^{2+}$, and substrate, i.e. geranyl diphosphate. The aqueous layer is overlaid with pentane to trap volatile compounds. After incubation, the assay mixture is extracted with pentane a second time, both pentane fractions are pooled, concentrated and analyzed by gas chromatography to quantify ocimene/myrcene production.

Farnesene synthases are generally classified into two different groups, i.e. alpha-farnesene synthases (EC 4.2.3.46) and beta farnesene synthases (EC 4.2.3.47). Alpha-farnesene synthases (EC 4.2.3.46) naturally catalyze the following reaction:

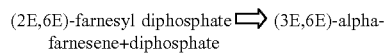

(2E,6E)-farnesyl diphosphate ⟹ (3E,6E)-alpha-farnesene+diphosphate

This enzyme occurs in a number of organisms, in particular in plants, for example in *Malus×domestica* (UniProt accession numbers Q84LB2, B2ZZ11, Q6Q2J2, Q6QWJ1 and Q32WI2), *Populus trichocarpa*, *Arabidopsis thaliana* (UniProt accession numbers A4FVP2 and P0CJ43), *Cucumis melo* (UniProt accession number B2KSJ5) and *Actinidia deliciosa* (UniProt accession number C7SHN9). In principle, any known alpha-farnesene synthase can be employed in the method according to the invention. In a preferred embodiment, the alpha-farnesene synthase employed in a method according to the present invention is an alpha-farnesene synthase from *Malus×domestica* (UniProt accession numbers Q84LB2, B2ZZ11, Q6Q2J2, Q6QWJ1 and Q32WI2; see also Green et al.; Photochemistry 68 (2007), 176-188).

Beta-farnesene synthases (EC 4.2.3.47) naturally catalyze the following reaction:

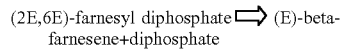

(2E,6E)-farnesyl diphosphate ⟹ (E)-beta-farnesene+diphosphate

This enzyme occurs in a number of organisms, in particular in plants and in bacteria, for example in *Artemisia annua* (UniProt accession number Q4VM12), *Citrus junos* (UniProt accession number Q94JS8), *Oryza sativa* (UniProt accession number Q0J7R9), *Pinus sylvestris* (UniProt accession number D7PCH9), *Zea diploperennis* (UniProt accession number C7E5V9), *Zea mays* (UniProt accession numbers Q2NM15, C7E5V8 and C7E5V7), *Zea perennis* (UniProt accession number C7E5W0) and *Streptococcus coelicolor* (Zhao et al., J. Biol. Chem. 284 (2009), 36711-36719). In principle, any known beta-farnesene synthase can be employed in the method according to the invention. In a preferred embodiment, the beta-farnesene synthase employed in a method according to the present invention is a beta-farnesene synthase from *Mentha piperita* (Crock et al.; Proc. Natl. Acad. Sci. USA 94 (1997), 12833-12838).

Methods for the determination of farnesene synthase activity are known in the art and are described, for example, in Green et al. (Phytochemistry 68 (2007), 176-188). In a typical assay farnesene synthase is added to an assay buffer containing 50 mM BisTrisPropane (BTP) (pH 7.5), 10% (v/v) glycerol, 5 mM DTT. Tritiated farnesyl diphosphate and metal ions are added. Assays containing the protein are overlaid with 0.5 ml pentane and incubated for 1 h at 30° C. with gentle shaking. Following addition of 20 mM EDTA (final concentration) to stop enzymatic activity an aliquot of the pentane is removed for scintillation analysis. The olefin products are also analyzed by GC-MS.

Pinene synthase (EC 4.2.3.14) is an enzyme which naturally catalyzes the following reaction:

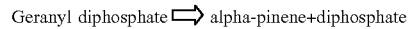

Geranyl diphosphate ⟹ alpha-pinene+diphosphate

This enzyme occurs in a number of organisms, in particular in plants, for example in *Abies grandis* (UniProt accession number 0244475), *Artemisia annua*, *Chamaecyparis formosensis* (UniProt accession number C3RSF5), *Salvia officinalis* and *Picea sitchensis* (UniProt accession number Q6XDB5).

For the enzyme from *Abies grandis* a particular reaction was also observed (Schwab et al., Arch. Biochem. Biophys. 392 (2001), 123-136), namely the following:

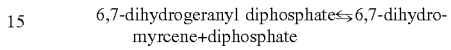

6,7-dihydrogeranyl diphosphate⇌6,7-dihydro-myrcene+diphosphate

In principle, any known pinene synthase can be employed in the method according to the invention. In a preferred embodiment, the pinene synthase employed in a method according to the present invention is a pinene synthase from *Abies grandis* (UniProt accession number 0244475; Schwab et al., Arch. Biochem. Biophys. 392 (2001), 123-136).

Methods for the determination of pinene synthase activity are known in the art and are described, for example, in Schwab et al. (Archives of Biochemistry and Biophysics 392 (2001), 123-136). In a typical assay, the assay mixture for pinene synthase consists of 2 ml assay buffer (50 mM Tris/HCl, pH 7.5, 500 mM KCl, 1 mM MnCl2, 5 mM dithiothreitol, 0.05% NaHSO3, and 10% glycerol) containing 1 mg of the purified protein. The reaction is initiated in a Teflon-sealed screw-capped vial by the addition of 300 mM substrate. Following incubation at 25° C. for variable periods (0.5-24 h), the mixture is extracted with 1 ml of diethyl ether. The biphasic mixture is vigorously mixed and then centrifuged to separate the phases. The organic extract is dried (MgSO4) and subjected to GC-MS and MDGC analysis.

As indicated above, it is also possible to employ other monoterpene synthases in a method according to the invention, for example the monoterpene synthase from *Melaleuca alternifolia* described in Shelton et al. (Plant Physiol. Biochem. 42 (2004), 875-882) or the monoterpene synthase from *Eucalyptus globulus* (UniProt accession number Q0PCI4).

The present inventors have shown that different types of terpene synthases, e.g. isoprene synthases, (E,E)-alpha-farnesene synthases and beta-ocimene synthases from different plant organisms are able to convert propan-2-yl into propylene (see Example 2).

The reactions catalyzed by the various terpene synthases, in particular the terpene synthases mentioned above, show certain common features. For example, the reactions catalyzed by isoprene synthases, by myrcene/ocimene synthases, by farnesene synthases, by pinene synthase and by other monoterpene synthases, respectively, are all believed to proceed through a common mechanism in which, in a first step a carbocation is created by elimination of the diphosphate ($PP_i$), which is then followed by direct deprotonation so as to form the corresponding diene.

It could be shown by the present inventors that enzymes which belong to the family of terpene synthases are able to carry out the corresponding reaction by using an alkyl monoester as specified in formula (I), above, so as to form a monoalkene. The natural reaction catalyzed by the terpene synthases is depicted in a schematic form in FIG. 1 as well as the reaction when it is applied to an alkyl monoester as defined in formula (I), above.

As mentioned above, in another preferred embodiment the enzyme employed in a method according to the present invention is an enzyme which can be classified as belonging to the prenyltransferase family. Prenyltransferases are a class of enzymes that transfer allylic prenyl groups to acceptor molecules. Prenyltransferases can be classified as EC 2.5.1. The prenyltransferases and terpene synthases are mechanistically linked by a common early step in their catalyzed reactions. The reaction catalyzed by prenyltransferases starts with the elimination of the diphosphate ion from an allylic diphosphate to form an allylic cation. Namely, both groups of enzymes employ a divalent metal ion (coordinated by a conserved DDXXD/E motif) to facilitate cleavage of the pyrophosphate bond of an allylic diphosphate substrate (Christianson D W Chem Rev. 106 (2006), 3412-3442). In the Gene Ontology database these enzymes are identified under the identification number GO:0004659. Prenyltransferases are commonly divided into two classes, i.e. cis (or Z) and trans (or E) depending upon the stereochemistry of the resulting products. In the scope of the present invention both classes can be employed. The term "prenyltransferase" as used herein comprises in particular the following three main classes of prenyltransferases:

Isoprenyl pyrophosphate synthases, which catalyze the chain elongation of allylic pyrophosphate substrates via consecutive condensation reactions with isopentenyl pyrophosphate to generate linear polymers with defined chain lengths;

Protein prenyltransferases, which catalyze the transfer of an isoprenyl pyrophosphate to a protein or peptide; and Prenyltransferases which catalyze the cyclization of isoprenyl pyrophosphate (see Liang et al., Eur. J. Biochem. 269 (2002), 3339-3354, for a review). Prenyltransferases have been studied in detail as regards their structure and function and crystal data as well as information on the reaction mechanism are available for a variety of prenyltransferases (see e.g. Chang et al., J. Biol. Chem. 278 (2003), 29298-29397; Chang et al., Protein Science 13 (2004), 971-977).

In principle, any prenyltransferase can be employed in the method according to the present invention, in particular any prenyltransferase of the three classes mentioned above.

In a preferred embodiment the prenyltransferase employed in a method according to the present invention is a dimethylallyltranstransferase (EC 2.5.1.1), a (2E,6E)-farnesyl diphosphate synthase (EC 2.5.1.10), a geranylgeranyl diphosphate synthase (EC 2.5.1.29), a ditrans,polycis-undecaprenyl-diphosphate synthase [(2E,6E)-farnesyl-diphosphate specific (EC 2.5.1.31) or a squalen synthase (EC 2.5.1.21).

Dimethylallyltranstransferase catalyzes the reaction:

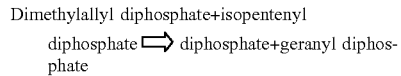

Dimethylallyl diphosphate+isopentenyl diphosphate ⟹ diphosphate+geranyl diphosphate In principle any dimethylallyltranstransferase can be employed in the method according to the invention. This enzyme is known from a number of organisms, including animals, plants, fungi and bacteria and has been described, e.g., in *Sacharomyces cerevisiae, Rhizobium loti, Acyrthosiphon pisum, Geobacillus stearothermophilus, Ips pini, Mentha×piperita, Myzus persicae, Picea abies, Gallus gallus, Homo sapiens* and *Sus scrofa*.

(2E,6E)-farnesyl diphosphate synthase catalyzes the reaction:

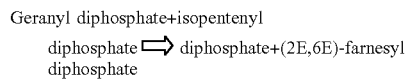

Geranyl diphosphate+isopentenyl diphosphate ⟹ diphosphate+(2E,6E)-farnesyl diphosphate In principle any 2E,6E)-farnesyl diphosphate synthase can be employed in the method according to the invention. This enzyme is known from a number of organisms, including animals, plants, fungi and bacteria and has been described, e.g., in *Streptomyces argenteolus, Mycobacterium tuberculosis, E. coli, Geobacillus stearothermophilus, Abies grandis, Acyrthosiphon grandis, Anthonomus grandis, Artemisia tridentate, Bacillus subtilis, Myzus persica, Ricinus communis, Panax ginseng, Plasmodium vivax, S. cerevisiae, Toxoplasma gondii, Trypanosoma cruzi, Rattus norvegicus, Gallus gallus, Homo sapiens* and *Sus scrofa*.

Geranylgeranyl diphosphate synthase catalyzes the reaction:

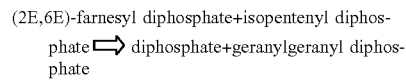

(2E,6E)-farnesyl diphosphate+isopentenyl diphosphate ⟹ diphosphate+geranylgeranyl diphosphate In principle any geranylgeranyl diphosphate synthase can be employed in the method according to the invention. This enzyme is known from a multitude of organisms, including animals, plants, fungi and bacteria and has been described, e.g., in *Methanothermobacter thermautotrophicus, S. cerevisiae, Schizosaccharomyces pombe, Sulfolobus acidocaldarius, Thermus tthermopilus, Toxoplasma gondii, Thermococcus kodakarensis, Ginko biloba, Taxus×media, Cistus creticus, Sinapis alba, Zea mays, Solanum lycopersicum, Rattus norvegicus, Homo sapiens* and *Mus musculus* to name just some.

Ditrans,polycis-undecaprenyl-diphosphate synthase [(2E,6E)-farnesyl-diphosphate specific] catalyzes the reaction:

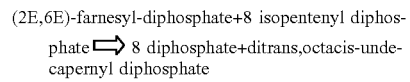

(2E,6E)-farnesyl-diphosphate+8 isopentenyl diphosphate ⟹ 8 diphosphate+ditrans,octacis-undecapernyl diphosphate In principle any ditrans,polycis-undecaprenyl-diphosphate synthase [(2E,6E)-farnesyl-diphosphate specific] can be employed in the method according to the invention. This enzyme is known from several organisms, including fungi and bacteria and has been described, e.g., in *Micrococcus luteus, E. coli, Haemophilus influenza, Streptococcus pneumonia, Bacillus subtilis, Helicobacter pyloris, Lactobacillus plantarum, Salmonella Newington* and *S. cerevisiae*.

Squalen synthase catalyzes the reaction:

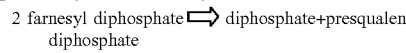

2 farnesyl diphosphate ⟹ diphosphate+presqualen diphosphate

In principle any squalen synthase can be employed in the method according to the invention. This enzyme is known from a multitude of organisms, including animals, plants, fungi and bacteria and has been described, e.g., in *Trypanosoma cruzi, S. cerevisiae, Arabidopsis thaliana, Euphorbia tirucalli, Panax ginseng, Cavia porcellus, Macaca mulatta, Mus musculus, Rattus norvegicus, Oryctolagus cuniculus, Cricetus cricetus* and *Homo sapiens* to name just some.

The alkyl monoester which is used as a starting material in a method according to the present invention is a compound of formula (I)

(I)

wherein $R^1$, $R^2$, $R^3$ and $R^4$ are each independently selected from hydrogen, methyl or ethyl; and wherein X is selected from:

O—PO₃H₂ monophosphate
O—PO₂H—O—PO₃H₂ diphosphate
O—SO₃H sulfate

It is particularly preferred that the alkyl monoester of formula (I)) is selected from: ethyl diphosphate, propan-1-yl diphosphate (propyl diphosphate), propan-2-yl diphosphate (isopropyl diphosphate), butan-1-yl diphosphate (1-butyl diphosphate), butan-2-yl diphosphate (2-butyl diphosphate), 2-methylpropan-1-yl diphosphate (isobutyl diphosphate), 1,1-dimethylethyl diphosphate (tert-butyl diphosphate), ethyl monophosphate, propan-1-yl monophosphate (propyl monophosphate), propan-2-yl monophosphate (isopropyl monophosphate), butan-1-yl monophosphate (1-butyl monophosphate), (2-butyl monophosphate), (isobutyl monophosphate), (tert-butyl monophosphate), ethyl sulfate, propan-1-yl sulfate (propyl sulfate), propan-2-yl sulfate (isopropyl sulfate), butan-1-yl sulfate (1-butyl sulfate), butan-2-yl sulfate (2-butyl sulfate), 2-methylpropan-1-yl sulfate (isobutyl sulfate) and 1,1-dimethylethyl sulfate (tert-butyl sulfate).

The following Table 1 gives an overview over alkyl monoesters preferably to be employed in the method according to the invention and the resulting alkenes:

TABLE 1

| No. | Alkyl monoester | Monoalkene |
|---|---|---|
| 1 | ethyl diphosphate | ethene (i.e. ethylene) |
| 2 | propan-1-yl diphosphate (propyl diphosphate) | propene (i.e. propylene; methylethylene) |
| 3 | propan-2-yl diphosphate (isopropyl diphosphate) | propene (i.e. propylene; methylethylene) |
| 4 | butan-1-yl diphosphate (1-butyl diphosphate) | but-1-ene (i.e. α-butylene) |
| 5 | butan-2-yl diphosphate (2-butyl diphosphate) | but-1-ene (i.e. α-butylene) and but-2-ene (i.e. β-butylene) |
| 6 | 2-methylpropan-1-yl diphosphate (isobutyl diphosphate) | 2-methylprop-1-ene (isobutene); |
| 7 | 1,1-dimethylethyl diphosphate (tert-butyl diphosphate) | 2-methylprop-1-ene (i.e. isobutene; isobutylene) |
| 8 | ethyl monophosphate | ethene (i.e. ethylene) |
| 9 | propan-1-yl monophosphate (propyl monophosphate) | propene (i.e. propylene; methylethylene) |
| 10 | propan-2-yl monophosphate (isopropyl monophosphate) | propene (i.e. propylene; methylethylene) |
| 11 | butan-1-yl monophosphate (1-butyl monophosphate) | but-1-ene (i.e. α-butylene) |
| 12 | butan-2-yl monophosphate (2-butyl monophosphate) | but-1-ene (i.e. α-butylene) and but-2-ene (i.e. β-butylene) |
| 13 | 2-methylpropan-1-yl monophosphate (isobutyl monophosphate) | 2-methylprop-1-ene (i.e. isobutene; isobutylene) |
| 14 | 1,1-dimethylethyl monophosphate (tert-butyl monophosphate) | 2-methylprop-1-ene (isobutene) |
| 15 | ethyl sulfate | ethene (i.e. ethylene) |
| 16 | propan-1-yl sulfate (propyl sulfate) | propene (i.e. propylene; methylethylene) |
| 17 | propan-2-yl sulfate (isopropyl sulfate) | propene (i.e. propylene; methylethylene) |
| 18 | butan-1-yl sulfate (1-butyl sulfate) | but-1-ene (i.e. α-butylene) |
| 19 | butan-2-yl sulfate (2-butyl sulfate) | but-2-ene (i.e. β-butylene) |
| 20 | 2-methylpropan-1-yl sulfate (isobutyl sulfate) | 2-methylprop-1-ene (i.e. isobutene; isobutylene) |
| 21 | 1,1-dimethylethyl sulfate (tert-butyl sulfate) | 2-methylprop-1-ene (i.e. isobutene; isobutylene) |

In one preferred embodiment the alkyl monoester according to formula (I) is an alkyl monoester in which group X is diphosphate and $R^1$, $R^2$, $R^3$ and $R^4$ are each independently selected from hydrogen, methyl or ethyl. In a particularly preferred embodiment the alkyl monoester is selected from the group consisting of ethyl diphosphate, propan-1-yl diphosphate (propyl diphosphate), propan-2-yl diphosphate (isopropyl diphosphate), butan-1-yl diphosphate (1-butyl diphosphate), butan-2-yl diphosphate (2-butyl diphosphate), 2-methylpropan-1-yl diphosphate (isobutyl diphosphate) and 1,1-dimethylethyl diphosphate (tert-butyl diphosphate).

In another preferred embodiment the alkyl monoester according to formula (I) is an alkyl monoester in which group X is phosphate and $R^1$, $R^2$, $R^3$ and $R^4$ are each independently selected from hydrogen, methyl or ethyl. In a particularly preferred embodiment the alkyl monoester is selected from the group consisting of ethyl monophosphate, propan-1-yl monophosphate (propyl monophosphate), propan-2-yl monophosphate (isopropyl monophosphate), butan-1-yl monophosphate (1-butyl monophosphate), (2-butyl monophosphate), (isobutyl monophosphate) and (tert-butyl monophosphate).

In another preferred embodiment the alkyl monoester according to formula (I) is an alkyl monoester in which group X is sulfate and $R^1$, $R^2$, $R^3$ and $R^4$ are each independently selected from hydrogen, methyl or ethyl. In a particularly preferred embodiment the alkyl monoester is selected from the group consisting of ethyl sulfate, propan-1-yl sulfate (propyl sulfate), propan-2-yl sulfate (isopropyl sulfate), butan-1-yl sulfate (1-butyl sulfate), butan-2-yl sulfate (2-butyl sulfate), 2-methylpropan-1-yl sulfate (isobutyl sulfate) and 1,1-dimethylethyl sulfate (tert-butyl sulfate).

In a particularly preferred embodiment the monoalkene to be produced is propylene and the alky monoester according to formula (I) is propan-1-yl diphosphate (propyl diphosphate), propan-2-yl diphosphate (isopropyl diphosphate), propan-1-yl monophosphate (propyl monophosphate), propan-2-yl monophosphate (isopropyl monophosphate), propan-1-yl sulfate (propyl sulfate) or propan-2-yl sulfate (isopropyl sulfate).

It is to be understood that the alkyl monoester to be used in the method according to the invention may also be a mixture of different compounds of formula (I).

In a preferred embodiment of the present invention the enzyme employed in a method according to the present invention is an enzyme comprising an amino acid sequence selected from the group consisting of SEQ ID NOs: 1 to 10 or a sequence which is at least n % identical to any of SEQ ID NOs: 1 to 10 and having the activity of a terpene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. The term "sequence identity" preferably means the same amino acid residues in the same N- to C-terminal direction.

In one preferred embodiment, the enzyme employed in a method according to the present invention is an enzyme comprising an amino acid sequence as shown in SEQ ID NO: 1 or a sequence which is at least n % identical to SEQ ID NO: 1 and having the activity of an isoprene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 1 shows the isoprene synthase from *Pueraris monotana* var. *lobata* (Uniprot Q6EJ97).

In another preferred embodiment, the enzyme employed in a method according to the present invention is an enzyme comprising an amino acid sequence as shown in SEQ ID NO: 2 or a sequence which is at least n % identical to SEQ ID NO: 2 and having the activity of an (E)-beta-ocimene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 2 shows the (E)-beta-ocimene synthase from *Vitis vinifera* (Uniprot E5GAG5).

In another preferred embodiment, the enzyme employed in a method according to the present invention is an enzyme comprising an amino acid sequence as shown in SEQ ID NO: 3 or a sequence which is at least n % identical to SEQ ID NO: 3 and having the activity of an (E,E)-alpha-farnesene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 3 shows the (E,E)-alpha-farnesene synthase from *Malus domestica* (Uniprot Q84LB2).

In another preferred embodiment, the enzyme employed in a method according to the present invention is an enzyme comprising an amino acid sequence as shown in SEQ ID NO: 4 or a sequence which is at least n % identical to SEQ ID NO: 4 and having the activity of an monoterpene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 4 shows a monoterpene synthase from *Melaleuca alternifolia* (Uniprot Q7Y1V1).

In another preferred embodiment, the enzyme employed in a method according to the present invention is an enzyme comprising an amino acid sequence as shown in SEQ ID NO: 5 or a sequence which is at least n % identical to SEQ ID NO: 5 and having the activity of an beta-ocimene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 5 shows a beta-ocimene synthase from *Phaseolus lunatus* (Uniprot B1P189).

In another preferred embodiment, the enzyme employed in a method according to the present invention is an enzyme comprising an amino acid sequence as shown in SEQ ID NO: 6 or a sequence which is at least n % identical to SEQ ID NO: 6 and having the activity of an pinene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 6 shows a chloroplastic pinene synthase from *Abies grandis* (Uniprot 024475).

In another preferred embodiment, the enzyme employed in a method according to the present invention is an enzyme comprising an amino acid sequence as shown in SEQ ID NO: 7 or a sequence which is at least n % identical to SEQ ID NO: 7 and having the activity of an pentalenene synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 7 shows a pentalenene synthase from *Streptomyces* sp. (strain UC5319) (Uniprot P33247).

In another preferred embodiment, the enzyme employed in a method according to the present invention is an enzyme comprising an amino acid sequence as shown in SEQ ID NO: 8 or a sequence which is at least n % identical to SEQ ID NO: 8 and having the activity of an germacrene-D synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 8 shows a germacrene-D synthase from *Ocimum basilicum* (Uniprot Q5SBP6).

In another preferred embodiment, the enzyme employed in a method according to the present invention is an enzyme comprising an amino acid sequence as shown in SEQ ID NO: 9 or a sequence which is at least n % identical to SEQ ID NO: 9 and having the activity of an beta-eudesmol synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 9 shows a beta-eudesmol synthase from *Zingiber zerumbet* (Uniprot B1B1U4).

In another preferred embodiment, the enzyme employed in a method according to the present invention is an enzyme comprising an amino acid sequence as shown in SEQ ID NO: 10 or a sequence which is at least n % identical to SEQ ID NO: 10 and having the activity of an squalene-hopene cyclase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 10 shows a squalene-hopene cyclase from *Alicyclobacillus acidocaldarius* subsp. *acidocaldarius* (Uniprot P33247).

Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Other algorithms which can be used for calculating sequence identity are those of Needleman and Wunsch or of Smith and Watermann. For sequence comparisons the program PileUp (Feng and Doolittle, J. Mol. Evolution 25 (1987), 351-360; Higgins et al., CABIOS 5 (1989), 151-153) or the programs Gap and Best Fit (Needleman and Wunsch, J. Mol. Biol. 48 (1970), 443-453; Smith and Waterman, Adv. Appl. Math. 2 (1981), 482-489) can be used, which are contained in the GCG software package (Genetics Computer Group, 575 Science Drive, Madison, Wis., USA). Preferably, the settings which are used are the standard settings for sequence comparisons.

Preferably, the degree of identity is calculated over the complete length of the sequence.

The enzyme, preferably the terpene synthase or prenyltransferase, employed in the process according to the invention can be a naturally occurring enzyme or it can be an enzyme which is derived from a naturally occurring enzyme, preferably a terpene synthase or a prenyltransferase, e.g. by the introduction of mutations or other alterations which, e.g., alter or improve the enzymatic activity, the stability, etc. The term "terpene synthase" or "a protein/enzyme having the activity of a terpene synthase" in the context of the present application also covers enzymes which are derived from a terpene synthase, which are capable of eliminating the phosphorus or sulfur containing molecule XH from the alkyl monoester of formula (I) so as to convert it into a monoalkene but which only have a low affinity to their natural substrate or do no longer accept their natural substrate.

Similarly, the term "prenyltransferase" or "a protein/enzyme having the activity of a prenyltransferase" in the context of the present application also covers enzymes which are derived from a prenyltransferase, which are capable of eliminating the phosphorus or sulfur containing molecule XH from the alkyl monoester of formula (I) so as to convert it into a monoalkene but which only have a low affinity to their natural substrate or do no longer accept their natural substrate.

Thus, the term "terpene synthase" or "a protein/enzyme having the activity of a terpene synthase" in the context of the present application also covers enzymes which are derived from a terpene synthase as described herein-above, which are capable of eliminating the phosphorus or sulfur containing molecule XH from the alkyl monoester of formula (I) so as to convert it into a monoalkene but which only have a low affinity to their natural substrate as described herein-above in connection with the different terpene synthases or do no longer accept their natural substrate.

Accordingly, the term "prenyltransferase" or "a protein/enzyme having the activity of a prenyltransferase" in the context of the present application also covers enzymes which are derived from a prenyltransferase as described herein-above, which are capable of eliminating the phosphorus or sulfur containing molecule XH from the alkyl monoester of formula (I) so as to convert it into a monoalkene but which only have a low affinity to their natural substrate as described herein-above in connection with the different prenyltransferases or do no longer accept their natural substrate.

Such a modification of the preferred substrate of a terpene synthase or a prenyltransferase allows to improve the conversion of the alkyl monoester into the monoalkene and to reduce the production of unwanted by-product due to the action of the enzyme on their natural substrate(s). Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic engineering in prokaryotic cells, a nucleic acid molecule encoding an enzyme, preferably a terpene synthase or a prenyltransferase, can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme, preferably terpene synthase or prenyltransferase variants, are then tested for their enzymatic activity and in particular for their capacity to convert an alkyl monoester according to formula (I) into a monoalkene by eliminating molecule XH and prefer an alkyl monoester according to formula (I) as a substrate rather than their natural substrate(s) as described above in connection with the description of the different terpene synthases or prenyltransferases which can be used in the context of the present invention.

Assays for measuring the capacity of a terpene synthase or a prenyltransferase to convert an alkyl monoester according to formula (I) into a monoalkene by eliminating molecule XH are describe in the appended Examples.

Methods for identifying variants with improved enzymatic properties as regards the production of monoalkenes may also be carried out in the presence of a "cofactor" which allows for a steric and/or electronic complementation in the catalytic site of the enzyme due to the fact that the alkyl monoester used as a substrate may be shorter than the natural substrate of the terpene synthase or prenyltransferase employed in the method according to the invention. The cofactor may depend on the natural substrate of the enzyme to be employed in the method according to the invention.

Moreover, it is described for terpene synthases and for prenyltransferases that they require monovalent and/or divalent cations as co-factors (Green et al., J. Biol. Chem. 284 (2009), 8661-8669). Thus, in a further embodiment, a suitable amount of a suitable monovalent (e.g. $K^+$) and/or divalent cation is added to the reaction when carrying out the method according to the invention. The divalent cation is preferably $Mg^{2+}$ or $Mn^{2+}$.

The modified version of the enzyme, preferably a terpene synthase or a prenyltransferase, accepting an alkyl monoester according to formula (I), above as a substrate but having a low affinity to its natural substrate or no longer accepting its natural substrate may be derived from a naturally occurring enzyme, preferably a terpene synthase or a prenyltransferase, or from an already modified, optimized or synthetically produced enzyme, preferably a terpene synthase or a prenyltransferase.

The enzyme employed in the process according to the present invention can be a natural version of the protein or a synthetic protein as well as a protein which has been chemically synthesized or produced in a biological system or by recombinant processes. The enzyme may also be chemically modified, for example in order to improve its/their stability, resistance, e.g. to temperature, for facilitating its purification or its immobilization on a support. The enzyme may be used in isolated form, purified form, in immobilized form, as a crude or partially purified extract obtained from cells synthesizing the enzyme, as chemically synthesized enzyme, as recombinantly produced enzyme, in the form of microorganisms producing them etc.

The process according to the present invention may be carried out in vitro or in vivo. An in vitro reaction is understood to be a reaction in which no cells are employed, i.e. an acellular reaction.

For carrying out the process in vitro the substrates for the reaction and the enzyme are incubated under conditions (buffer, temperature, cofactors etc.) allowing the enzyme to be active and the enzymatic conversion to occur. The reaction is allowed to proceed for a time sufficient to produce the monoalkene. The production of the monoalkene can be detected by gas chromatography (GC) or GC/MS analysis.

The enzyme may be in any suitable form allowing the enzymatic reaction to take place. It may be purified or partially purified or in the form of crude cellular extracts or partially purified extracts. It is also possible that the enzyme is immobilized on a suitable carrier.

Since the alkyl monoester according to formula (I), above, used as a substrate may be shorter than the natural substrate used by the enzyme, it may be advantageous to add to the reaction mixture a "cofactor" which allows for a steric and/or electronic complementation in the catalytic site of the enzyme as mentioned above.

In general, if the monoalkene product is a gaseous and scarcely soluble in water under the conditions of temperature at which the process is conducted, the equilibrium of the reaction catalyzed by the enzyme employed is shifted and the reaction goes to completion in the direction of the formation of the gasous alkene, in particular if that gas is permanently removed from the reaction vessel.

In one particularly preferred embodiment, the enzyme (preferably a terpene synthase or a prenyltransferase) used in the process according to the invention is a thermophilic enzyme, i.e. an enzyme which is capable of catalyzing the reaction at elevated temperatures. The term "elevated temperatures" means temperatures above 37° C. Such enzymes can e.g. be obtained by mutagenizing available enzyme sequences, in particular terpene synthase sequences or prenyltransferase sequences, and testing them for an increased enzymatic activity under increased temperature conditions. The advantage of using an enzyme which is functional at elevated temperatures is that the produced monoalkene can immediately go into the gaseous phase and can be constantly removed from the reaction thereby driving the reaction into the direction of product formation. This advantage exists for all the produced monoalkenes which are in gaseous form at or below the temperature at which the reaction is carried out. Accordingly, in the method of the present invention the step of enzymatically converting an alkyl monoester according to formula (I), above, into a monoalkene by eliminating molecule XH is preferably carried out at an elevated temperature (i.e. at a temperature above 37° C., including a temperature above 37° C. and below 100° C., such as, e.g., at a temperature of 38° C., 40° C., 50° C., 70° C. or 90° C.) and the enzymatic conversion is catalyzed by a thermophilic enzyme as described herein above. The use of elevated temperatures also allows producing monoalkenes in a manner that they directly degas from the reaction mixture.

For carrying out the process in vivo use is made of a suitable organism/microorganism which is capable of expressing an enzyme as defined above, preferably a terpene synthase or a prenyltransferase. In a preferred embodiment, the organism/microorganism is capable of secreting the enzyme. In such an embodiment, the substrate for the reaction can be provided in the culture medium and the produced monoalkene can be recovered from the culture. In another preferred embodiment the organism/microorganism is also capable of producing the substrate, i.e. the alkyl monoester according to formula (I), above, to be converted.

Thus, in the case of this embodiment the method according to the invention is characterised in that the conversion of the alkyl monoester according to formula (I), above, into the monoalkene is realized in the presence of an organism/microorganism capable of expressing, preferably secreting, an enzyme as defined above, preferably a terpene synthase or a prenyltransferase. In another preferred embodiment of such a method the organism/microorganism is also capable of producing an alkyl monoester according to formula (I), above, which should be converted.

The term "which is capable of producing an alkyl monoester according to formula (I)" in the context of the present invention means that the organism/microorganism has the capacity to produce such an alkyl monoester within the cell due to the presence of enzymes providing enzymatic activities allowing the production of such an alkyl monoester from metabolic precursors. The organism/microorganism can be an organism/microorganism which naturally has the capacity to produce the corresponding alkyl monoester or it can be an organism/microorganism which has been genetically modified so as to be capable of producing the corresponding alkyl monoester.

In a preferred embodiment, the organism employed in the method according to the invention is an organism, preferably a microorganism, which has the capacity to produce the respective alkyl monoester according to formula (I), above, to be converted into the corresponding monoalkene and which is recombinant in the sense that it has further been genetically modified so as to express an enzyme as defined above, preferably a terpene synthase or a prenyltransferase as described above. The term "recombinant" in one embodiment means that the organism is genetically modified so as to contain a foreign nucleic acid molecule encoding said enzyme as defined above. In a preferred embodiment the organism has been genetically modified so as to contain a foreign nucleic acid molecule encoding said enzyme as defined above. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does not naturally occur in the respective organism/microorganism. Even more preferably, the promoter is an inducible promoter. Promoters for driving expression in different types of organisms, in particular in microorganisms, are well known to the person skilled in the art.

In another preferred embodiment the nucleic acid molecule is foreign to the organism/microorganism in that the encoded enzyme is not endogenous to the organism/microorganism, i.e. is naturally not expressed by the organism/microorganism when it is not genetically modified. In other words, the encoded enzyme is heterologous with respect to the organism/microorganism.

The term "recombinant" in another embodiment means that the organism is genetically modified in the regulatory region controlling the expression of an enzyme as defined above which naturally occurs in the organism so as to lead to an increase in expression of the respective enzyme in comparison to a corresponding non-genetically modified organism. The meaning of the term high "higher expression" is described further below.

Such a modification of a regulatory region can be achieved by methods known to the person skilled in the art. One example is to exchange the naturally occurring promoter by a promoter which allows for a higher expression or to modify the naturally occurring promoter so as to show a higher expression. Thus, in this embodiment the organism contains in the regulatory region of the gene encoding an enzyme as defined above a foreign nucleic acid molecule which naturally does not occur in the organism and which leads to a higher expression of the enzyme in comparison to a corresponding non-genetically modified organism.

The foreign nucleic acid molecule may be present in the organism/microorganism in extrachromosomal form, e.g. as a plasmid, or stably integrated in the chromosome. A stable integration is preferred.

In another preferred embodiment the organism/microorganism is characterized in that the expression/activity of an enzyme as defined above is higher in the organism/microorganism genetically modified with the foreign nucleic acid molecule in comparison to the corresponding non-genetically modified organism/microorganism. A "higher" expression/activity means that the expression/activity of the enzyme in the genetically modified microorganism is at least 10%, preferably at least 20%, more preferably at least 30% or 50%, even more preferably at least 70% or 80% and particularly preferred at least 90% or 100% higher than in the corresponding non-genetically modified organism/microorganism. In even more preferred embodiments the increase in expression/activity may be at least 150%, at least 200% or at least 500%. In particularly preferred embodiments the expression is at least 10-fold, more preferably at least 100-fold and even more preferred at least 1000-fold higher than in the corresponding non-genetically modified organism/microorganism.

The term "higher" expression/activity also covers the situation in which the corresponding non-genetically modified organism/microorganism does not express a corresponding enzyme so that the corresponding expression/activity in the non-genetically modified organism/microorganism is zero.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the described enzymes are known in the art and have already been described above.

Methods for preparing an organism which is genetically modified so as to produce an enzyme as described above, preferably a microorganism, are well known in the art. Thus, generally, the organism/microorganism is transformed with a DNA construct allowing expression of the respective enzyme in the microorganism. Such a construct normally comprises the coding sequence in question linked to regulatory sequences allowing transcription and translation in the respective host cell, e.g. a promoter and/or enhancer and/or transcription terminator and/or ribosome binding sites etc.

The term "organism" as used in the context of the present invention refers in general to any possible type of organism, in particular eukaryotic organisms, prokaryotic organisms and archaebacteria. The term includes animal, plants, fungi, bacteria and archaebacteria. The term also includes isolated cells or cell aggregates of such organisms, like tissue or calli.

In one preferred embodiment, the organism is a microorganism. The term "microorganism" in the context of the present invention refers to prokaryotic cells, in particular bacteria, as well as to fungi, such as yeasts, and also to algae and archaebacteria. In one preferred embodiment, the microorganism is a bacterium. In principle any bacterium can be used. Preferred bacteria to be employed in the process according to the invention are bacteria of the genus *Bacillus*, *Clostridium*, *Pseudomonas*, *Zymomonas* or *Escherichia*. In a particularly preferred embodiment the bacterium belongs to the genus *Escherichia* and even more preferred to the species *Escherichia coli*.

In another preferred embodiment the microorganism is a fungus, more preferably a fungus of the genus *Saccharomyces*, *Schizosaccharomyces*, *Aspergillus* or *Trichoderma* and even more preferably of the species *Saccharomyces cerevisiae*, *Schizosaccharomyces pombe*, *Aspergillus niger* or of the species *Trichoderma reesei*.

In still another preferred embodiment the microorganism is a photosynthetically active microorganism such as bacteria which are capable of carrying out photosynthesis or micro-algae.

In a particularly preferred embodiment the microorganism is an algae, more preferably an algae belonging to the diatomeae.

If microorganisms are used in the context of the method of the present invention, it is also conceivable to carry out the method according to the invention in a manner in which two types of microorganisms are employed, i.e. one type which produces the alkyl monoester according to formula (I), above, which should be converted into a monoalkene and one type which uses the alkyl monoester produced by the first type of microorganisms to convert it with the help of an enzyme as defined herein above into the respective monoalkene.

When the process according to the invention is carried out in vivo by using microorganisms providing the respective enzyme activity, the microorganisms are cultivated under suitable culture conditions allowing the occurrence of the enzymatic reaction. The specific culture conditions depend on the specific microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another preferred embodiment the organism employed in the method according to the invention is an organism which is capable of photosynthesis, such as a plant or microalgae. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as *eucalyptus*, poplar or rubber tree (*Hevea brasiliensis*).

In a particularly preferred embodiment the organism/microorganism employed in the method according to the invention is an organism/microorganism which is thermophilic in the sense that it can survive and catalyze the conversion of the alkyl monoester of formula (I) into a monoalkene of formula (II) at elevated temperatures. The term "elevated" temperature means a temperature over 37° C. Examples for such organism/microorganism are bacteria of the genus *Thermus*, e.g. *Thermus thermophilus* or *Thermus aquaticus*, or bacteria of the genus *Clostridium*, such as

*Clostridium thermocellum.* Other examples are microorganisms which are extremely heat-tolerant, e.g. microorganisms of the genus *Thermotoga*, such as *Thermotoga maritime*, or microorganisms of the genus *Aquifex*, such as *Aquifex aeolicus.*

The present invention also relates to an organism, preferably a microorganism, which is characterized by the following features:
(a) it is capable of producing an alkyl monoester according to formula (I), above; and
(b) it expresses an enzyme which is capable of catalyzing the conversion of said alkyl monoester into a monoalkene by elimination of molecule XH in formula (I), preferably a terpene synthase or a prenyltransferase.

As regards the source, nature, properties, sequence etc. of the enzyme expressed in the organism according to the invention, the same applies as has been set forth above in connection with the method according to the invention.

In one preferred embodiment, the organism according to the invention is an organism, preferably a microorganism, which naturally has the capacity to produce the alkyl monoester according to formula (I), above, i.e., feature (a) mentioned above is a feature which the organism, preferably microorganism, shows naturally.

In another preferred embodiment, the organism, preferably microorganism, according to the invention is a genetically modified organism/microorganism derived from an organism/microorganism which naturally does not produce the respective alkyl monoester according to formula (I), above, but which has been genetically modified so as to produce said alkyl monoester, i.e. by introducing the gene(s) necessary for allowing the production of the alkyl monoester in the organism/microorganism. In principle any organism/microorganism can be genetically modified in this way. The enzymes responsible for the synthesis of the respective alkyl monoester are generally known. Genes encoding corresponding enzymes are known in the art and can be used to genetically modify a given organism, preferably microorganism so as to produce the alkyl monoester.

In a further preferred embodiment the organism, preferably a microorganism, according to the invention is genetically modified so as to express an enzyme which is capable of catalyzing the conversion of an alkyl monoester according to formula (I), above, into a monoalkene as described herein-above. In this context, the term "recombinant" means in a first aspect that the organism contains a foreign nucleic acid molecule encoding a corresponding enzyme. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding said enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular microorganisms, are well known to the person skilled in the art.

In another preferred embodiment the nucleic acid molecule is foreign to the organism/microorganism in that the encoded enzyme is not endogenous to the organism/microorganism, i.e. is naturally not expressed by the organism/microorganism when it is not genetically modified. In other words, the encoded enzyme is heterologous with respect to the organism/microorganism.

The term "recombinant" in another aspect means that the organism is genetically modified in the regulatory region controlling the expression of an enzyme as defined above which naturally occurs in the organism so as to lead to an increase in expression of the respective enzyme in comparison to a corresponding non-genetically modified organism. The meaning of the term high "higher expression" is described further below.

Such a modification of a regulatory region can be achieved by methods known to the person skilled in the art. One example is to exchange the naturally occurring promoter by a promoter which allows for a higher expression or to modify the naturally occurring promoter so as to show a higher expression. Thus, in this embodiment the organism contains in the regulatory region of the gene encoding an enzyme as defined above a foreign nucleic acid molecule which naturally does not occur in the organism and which leads to a higher expression of the enzyme in comparison to a corresponding non-genetically modified organism.

In a further preferred embodiment the organism/microorganism is characterized in that the expression/activity of the enzyme is higher in the organism/microorganism genetically modified with the foreign nucleic acid molecule in comparison to the corresponding non-genetically modified organism/microorganism. A "higher" expression/activity means that the expression/activity of the enzyme in the genetically modified organism/microorganism is at least 10%, preferably at least 20%, more preferably at least 30% or 50%, even more preferably at least 70% or 80% and particularly preferred at least 90% or 100% higher than in the corresponding non-genetically modified organism/microorganism. In even more preferred embodiments the increase in expression/activity may be at least 150%, at least 200% or at least 500%. In particularly preferred embodiments the expression is at least 10-fold, more preferably at least 100-fold and even more preferred at least 1000-fold higher than in the corresponding non-genetically modified organism/microorganism.

The term "higher" expression/activity also covers the situation in which the corresponding non-genetically modified organism/microorganism does not express a corresponding enzyme so that the corresponding expression/activity in the non-genetically modified organism/microorganism is zero.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of an enzyme as described herein are known in the art and have already been described above.

The term "organism" as used in the context of the present invention refers in general to any possible type of organism, in particular eukaryotic organisms, prokaryotic organisms and archaebacteria. The term includes animal, plants, fungi, bacteria and archaebacteria. The term also includes isolated cells or cell aggregates of such organisms, like tissue or calli.

In one preferred embodiment, the organism is a microorganism. The term "microorganism" in the context of the present invention refers to prokaryotic cells, in particular bacteria, as well as to fungi, such as yeasts, and also to algae and archaebacteria. In one preferred embodiment, the microorganism is a bacterium. In principle any bacterium can be used. Preferred bacteria to be employed in the process according to the invention are bacteria of the genus *Bacillus, Clostridium, Pseudomonas, Zymomonas* or *Escherichia*. In a particularly preferred embodiment the bacterium belongs to the genus *Escherichia* and even more preferred to the species *Escherichia coli*.

In another preferred embodiment the microorganism is a fungus, more preferably a fungus of the genus *Saccharomyces, Schizosaccharomyces, Aspergillus* or *Trichoderma* and even more preferably of the species *Saccharomyces cerevisiae, Schizosaccharomyces pombe, Aspergillus niger* or of the species *Trichoderma reesei*.

In still another preferred embodiment the microorganism is a photosynthetically active microorganism such as bacteria which are capable of carrying out photosynthesis or micro-algae.

In a particularly preferred embodiment the microorganism is an algae, more preferably an algae from the genus belonging to the diatomeae.

In another preferred embodiment the organism according to the invention is an organism which is capable of photosynthesis, such as a plant or micro-algae. In principle, it can be any possible plant, i.e. a monocotyledonous plant or a dicotyledonous plant. It is preferably a plant which can be cultivated on an agriculturally meaningful scale and which allows to produce large amounts of biomass. Examples are grasses like *Lolium*, cereals like rye, barley, oat, millet, maize, other starch storing plants like potato or sugar storing plants like sugar cane or sugar beet. Conceivable is also the use of tobacco or of vegetable plants such as tomato, pepper, cucumber, egg plant etc. In another preferred embodiment the plant is an oil storing plants such as rape seed, olives etc. Also conceivable is the use of trees, in particular fast growing trees such as *eucalyptus*, poplar or rubber tree (*Hevea brasiliensis*).

In a particularly preferred embodiment the organism/microorganism employed in the method according to the invention is an organism/microorganism which is thermophilic in the sense that it can survive and catalyze the dehydration of the alkyl monoester of formula (I) into a monoalkene of formula (II) at elevated temperatures. The term "elevated" temperature means a temperature over 37° C. Examples for such organism/microorganism are bacteria of the genus *Thermus*, e.g. *Thermus thermophilus* or *Thermus aquaticus*, or bacteria of the genus *Clostridium*, such as *Clostridium thermocellum*. Other examples are microorganisms which are extremely heat-tolerant, e.g. microorganisms of the genus *Thermotoga*, such as *Thermotoga maritime*, or microorganisms of the genus *Aquifex*, such as *Aquifex aeolicus*.

The present invention also relates to the use of an organism which expresses an enzyme as described herein-above, preferably a terpene synthase or a prenyltransferase, for converting an alkyl monoester according to formula (I), above into a monoalkene according to formula (II), above, by enzymatically eliminating molecule XH as specified in formula (I).

Preferably, in such a use, the organism is an organism according to the present invention, i.e. a (micro)organism, which is characterized by the following features:
(a) it is capable of producing an alkyl monoester according to formula (I), above; and
(b) it expresses an enzyme which is capable of catalyzing the conversion of said alkyl monoester into a monoalkene by elimination of molecule XH in formula (I), preferably a terpene synthase or a prenyltransferase.

I.e., the present invention also relates to the use of an organism/microorganism according to the invention for the production of a monoalkene from the respective alkyl monoester.

The present invention also relates to a composition comprising an organism according to the present invention.

Moreover, the present invention also relates to a composition comprising (i) an alkyl monoester according to formula (I), above; and (ii) an enzyme which is capable of catalyzing the conversion of said alkyl monoester into a monoalkene by elimination of molecule XH in formula (I), preferably a terpene synthase or a prenyltransferase, or an organism according to the present invention.

For the preferred embodiments of the enzyme and the organism, the same applies as has already been set forth above in connection with the method and the organism according to the invention.

Moreover, the present invention also relates to the use of a terpene synthase or of a prenyltransferase for the conversion of an alkyl monoester according to formula (I), above, into a monoalkene by elimination of molecule XH in formula (I).

For the preferred embodiments of the enzyme the same applies as has already been set forth above in connection with the method and the organism according to the invention.

Finally, the present invention also relates to the use of an alkyl monoester according to formula (I), above, for the production of a monoalkene, comprising the enzymatic conversion of the alkyl monoester into the monoalkene by elimination of molecule XH of formula (I).

In a preferred embodiment the enzymatic conversion is achieved by an enzyme as described above in connection with the method according to the invention, more preferably with a terpene synthase or a prenyltransferase and most preferably the conversion is achieved by the use of an organism according to the invention.

FIG. 1: shows in a schematic form the natural reaction catalyzed by the terpene synthases as well as the reaction when it is applied to an alkyl monoester as defined in formula (I), above.

Figure 2:
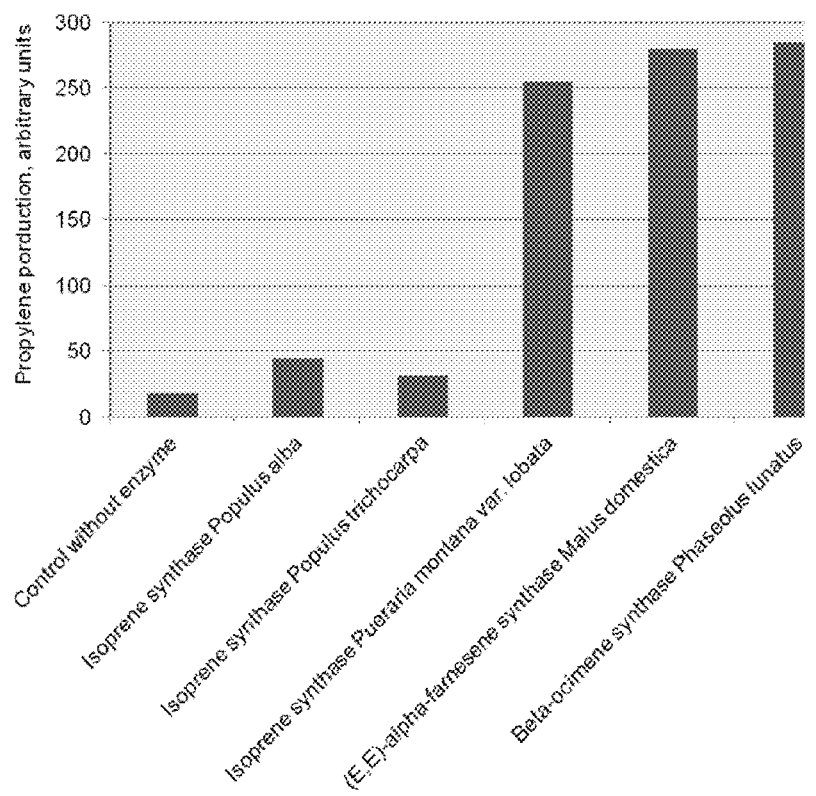

FIG. 2: shows propylene production from propan-2-yl diphosphate using terpene synthases (Example 2).

Figure 3A:
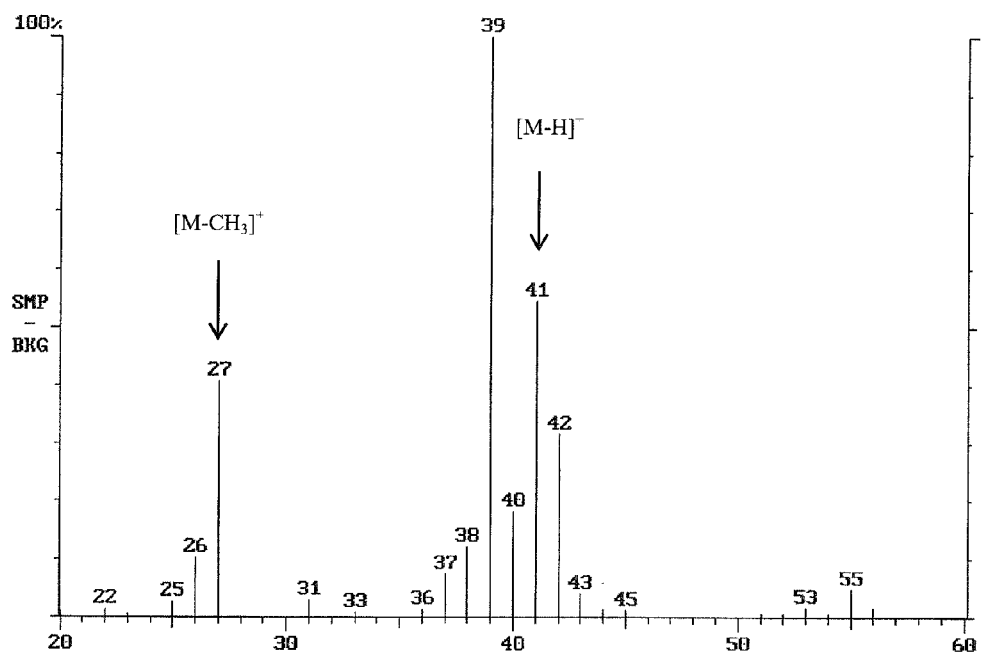
Figure 3B:
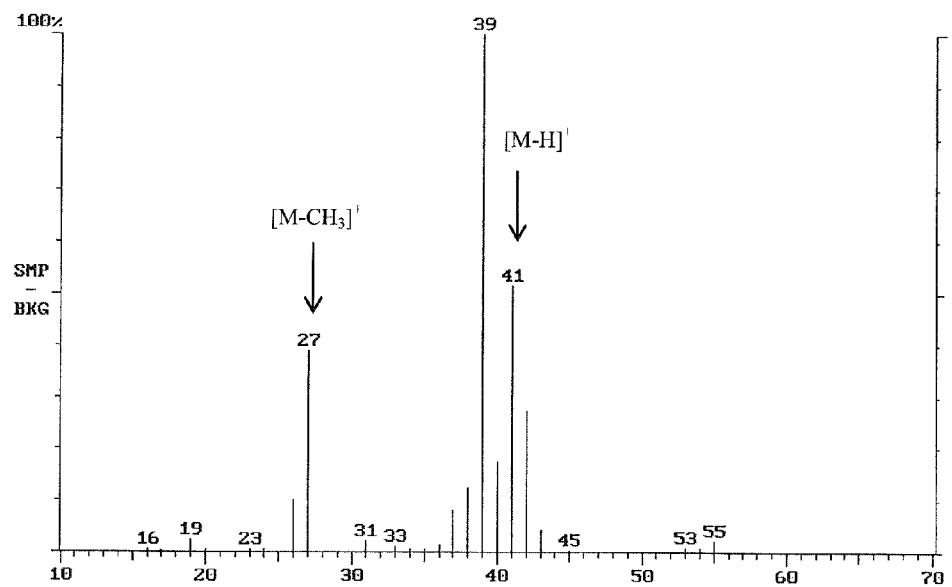

FIG. 3: shows mass spectrums of commercial propylene (a) and propylene produced from propan-2-yl diphosphate in enzymatic reaction catalyzed by isoprene synthase from *Pueraria montana* var. *lobata* (b). Characteristic ions of m/z 41 and 27, representing propylene were observed in both spectrums.

The following Examples serve to illustrate the invention.

EXAMPLE 1

Cloning, Expression and Purification of Enzymes

Cloning, Bacterial Cultures and Expression of Proteins.

The genes encoding the enzymes of interest were cloned in the pET 25b(+) vector (Novagen). Nucleotide sequences encoding chloroplast transit peptides in plant terpene synthases were removed, resulting in a DNA sequences encoding the mature proteins only. A stretch of 6 histidine codons was inserted after the methionine initiation codon to provide an affinity tag for purification. Competent *E. coli* BL21 (DE3) cells (Novagen) were transformed with this vector by heat shock. The transformed cells were grown with shaking (160 rpm) on ZYM-5052 auto-induction medium (Studier F W, *Prot. Exp. Pur.* 41, (2005), 207-234) for 6 h at 37° C. and protein expression was continued at 28° C. or 18° C. overnight (approximately 16 h). The cells were collected by centrifugation at 4° C., 10,000 rpm for 20 min and the pellets were frozen at −80° C.

Protein Purification and Concentration.

The pellets from 200 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) were added. Cells were incubated 10 minutes at room temperature and then returned to ice for 20 minutes. Cell lysis was completed by sonication for 3×15 seconds. The bacterial extracts were then clarified by centrifugation at 4° C., 10,000 rpm for 20 min. The clarified bacterial lysates were loaded on PROTINO-1000 Ni-TED or Ni-IDA column (Macherey-Nagel) allowing adsorption of 6-His tagged proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated and desalted on Amicon Ultra-4 10 kDa filter unit (Millipore) and resuspended in 0.25 ml 50 mM Tris-HCl pH 7.5 containing 1 mM DTT and 10 mM $MgCl_2$. Protein concentrations were quantified by direct UV 280 nm measurement on the NanoDrop 1000 spectrophotometer (Thermo Scientific). The purity of proteins thus purified varied from 60% to 90%.

EXAMPLE 2

Propylene Production from Propan-2-yl Diphosphate with Purified Terpene Synthases The enzymatic assays were carried out under the following conditions:
50 mM Tris-HCl pH 7.5
100 mM $MgCl_2$
50 mM KCl
5 mM DTT
50 mM propan-2-yl diphosphate
5 mg of the terpene synthase was added to 0.5 ml of reaction mixture. An enzyme-free control reaction was carried out in parallel. Assays were incubated at 37° C. for 60 hours in a 1.5 ml sealed glass vial (Interchim) with shaking. One ml of the headspace phase was then collected and injected into a gas chromatograph Varian 430-GC equipped with a flame ionization detector (FID). Nitrogen was used as carrier gas with a flow rate of 1.5 mL/min. Volatile compounds were chromatographically separated on RT-Alumina Bond/$Na_2SO_4$ column (Restek) using an isothermal mode at 130° C. The enzymatic reaction product was identified by comparison with propylene standard (Sigma). Under these GC conditions, the retention time for propylene was 2.8 min. A significant production of propylene was observed with several purified terpene synthases (FIG. 2). Gas chromatography-mass spectrometry (GC-MS) was then used to confirm the identity of the product detected by gas chromatography with flame ionization. The samples were analyzed on a Varian 3400 CX gas chromatograph equipped with Varian Saturn 3 mass selective detector. The mass spectrum of propylene obtained by enzymatic conversion of propan-2-yl diphosphate was similar to the one of commercial propylene (FIG. 3).

EXAMPLE 3

Propylene Production from Propan-2-yl Monophosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM propan-2-yl diphosphate
5 mg of the terpene synthase is added to 0.5 ml of reaction mixture. An enzyme-free control reaction is carried out in parallel. Assays are incubated at 37° C. for 20-48 hours in a 1.5 ml sealed glass vial (Interchim) with shaking. Propylene production is analyzed using the GC/FID procedure described in example 2.

EXAMPLE 4

Ethylene Production from Ethyl Diphosphate with Purified Terpene Synthases

The enzymatic assays are carried out under the following conditions:
50 mM Tris-HCl pH 7.5
50-100 mM $MgCl_2$
20-50 mM KCl
2-5 mM DTT
50 mM ethyl diphosphate
5 mg of the terpene synthase is added to 0.5 ml of reaction mixture. An enzyme-free control reaction is carried out in parallel. Assays are incubated at 37° C. for 20-48 hours in a 1.5 ml sealed glass vial (Interchim) with shaking. One ml of the headspace phase is then collected and injected into a gas chromatograph Varian 430-GC equipped with a flame ionization detector (FID). Nitrogen is used as carrier gas with a flow rate of 1.5 mL/min. Volatile compounds are chromatographically separated on RT-Alumina Bond/$Na_2SO_4$ column (Restek) using an isothermal mode at 130° C. The enzymatic reaction product is identified by comparison with ethylene standard (Sigma). Under these GC conditions, the retention time for ethylene is 2.2 min

EXAMPLE 5

Propylene Production from Propan-1-yl Diphosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM propan-1-yl diphosphate
5 mg of the terpene synthase is added to 0.5 ml of reaction mixture. An enzyme-free control reaction is carried out in parallel. Assays are incubated at 37° C. for 20-48 hours in a

EXAMPLE 6

Isobutene Production from 2-Methylpropan-1-yl Diphosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM 2-methylpropan-1-yl diphosphate
5 mg of the terpene synthase is added to 0.5 ml of reaction mixture. An enzyme-free control reaction is carried out in parallel. Assays are incubated at 37° C. for 20-48 hours in a 1.5 ml sealed glass vial (Interchim) with shaking. One ml of the headspace phase is then collected and injected into a gas chromatograph Varian 430-GC equipped with a flame ionization detector (FID). Nitrogen is used as carrier gas with a flow rate of 1.5 mL/min. Volatile compounds are chromatographically separated on RT-Alumina Bond/$Na_2SO_4$ column (Restek) using an isothermal mode at 130° C. The enzymatic reaction product is identified by comparison with isobutene standard (Sigma). Under these GC conditions, the retention time for isobutene is 4.8 min.

EXAMPLE 7

Isobutene Production from 1,1-Dimethylethyl Diphosphate with Purified Terpene Synthases The enzymatic assays are carried out under the following conditions
50 mM Tris-HCl pH 7.5
50-100 mM $MgCl_2$
20-50 mM KCl
2-5 mM DTT
50 mM 1,1-dimethylethyl diphosphate
5 mg of the terpene synthase is added to 0.5 ml of reaction mixture. An enzyme-free control reaction is carried out in parallel. Assays are incubated at 37° C. for 20-48 hours in a 1.5 ml sealed glass vial (Interchim) with shaking. Isobutene production is analyzed using the GC/FID procedure described in Example 6.

EXAMPLE 8

But-1-Ene Production from Butan-1-yl Diphosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM butan-1-yl diphosphate
5 mg of the terpene synthase is added to 0.5 ml of reaction mixture. An enzyme-free control reaction is carried out in parallel. Assays are incubated at 37° C. for 20-48 hours in a 1.5 ml sealed glass vial (Interchim) with shaking. One ml of the headspace phase is then collected and injected into a gas chromatograph Varian 430-GC equipped with a flame ionization detector (FID). Nitrogen is used as carrier gas with a flow rate of 1.5 mL/min. Volatile compounds are chromatographically separated on RT-Alumina Bond/$Na_2SO_4$ column (Restek) using an isothermal mode at 130° C. The enzymatic reaction product is identified by comparison with but-1-ene standard (Sigma). Under these GC conditions, the retention time for but-1-ene is 4.3 min.

EXAMPLE 9

But-1-Ene and but-2-Ene Production from Butan-2-yl Diphosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM butan-2-yl diphosphate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. But-1-ene and but-2-ene production is analyzed using the GC/FID procedure described in Example 8. Under these GC conditions, the retention time for trans but-2-ene and cis but-2-ene are 4.2 min and 4.9 min, respectively.

EXAMPLE 10

Ethylene Production from Ethyl Monophosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM ethyl monophosphate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Ethylene production is analyzed using the GC/FID procedure described in Example 4.

EXAMPLE 11

Propylene Production from Propan-1-yl Monophosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM propan-1-yl monophosphate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Propylene production is analyzed using the GC/FID procedure described in Example 2.

EXAMPLE 12

Isobutene Production from 2-Methylpropan-1-yl Monophosphate with Purified Terpene Synthases The enzymatic assays are carried out under the following conditions:
50 mM HEPES pH 8.2
50-100 mM $MgCl_2$
20-50 mM KCl
2-5 mM DTT
50 mM 2-methylpropan-1-yl monophosphate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Isobutene production is analyzed using the GC/FID procedure described in example 6.

EXAMPLE 13

Isobutene Production from 1,1-Dimethylethyl Monophosphate with Purified Terpene Synthases The enzymatic assays are carried out under the following conditions
50 mM Tris-HCl pH 7.5
50-100 mM $MgCl_2$
20-50 mM KCl
2-5 mM DTT
50 mM 1,1-dimethylethyl monophosphate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Isobutene production is analyzed using the GC/FID procedure described in Example 6.

EXAMPLE 14

But-1-Ene Production from Butan-1-yl Monophosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM butan-1-yl monophosphate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. But-1-ene production is analyzed using the GC/FID procedure described in Example. 8

EXAMPLE 15

But-1-Ene and but-2-Ene Production from Butan-2-yl Monophosphate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM butan-2-yl monophosphate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. But-1-ene and but-2-ene production is analyzed using the GC/FID procedure described in Example 9.

EXAMPLE 16

Ethylene Production from Ethyl Sulfate with Purified Terpene Synthases

The enzymatic assays are carried out under the following conditions:
50 mM Tris-HCl pH 7.5
50-100 mM $MgCl_2$
20-50 mM KCl
2-5 mM DTT
50 mM ethyl sulfate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Ethylene production is analyzed using the GC/FID procedure described in Example 4.

EXAMPLE 17

Propylene Production from Propan-1-yl Sulfate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM propan-1-yl sulfate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Propylene production is analyzed using the GC/FID procedure described in Example 2.

EXAMPLE 18

Propylene Production from Propan-2-yl Sulfate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM propan-2-yl sulfate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Propylene production is analyzed using the GC/FID procedure described in Example 2.

EXAMPLE 19

Isobutene Production from 2-Methylpropan-1-yl Sulfate with Purified Terpene Synthases The enzymatic assays are carried out under the following conditions:
50 mM HEPES pH 8.2
50-100 mM $MgCl_2$
20-50 mM KCl
2-5 mM DTT
50 mM 2-methylpropan-1-yl sulfate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Isobutene production is analyzed using the GC/FID procedure described in Example 6.

EXAMPLE 20

Isobutene Production from 1,1-Dimethylethyl Sulfate with Purified Terpene Synthases The enzymatic assays are carried out under the following conditions
50 mM Tris-HCl pH 7.5
50-100 mM $MgCl_2$
20-50 mM KCl
2-5 mM DTT
50 mM 1,1-dimethylethyl sulfate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. Isobutene production is analyzed using the GC/FID procedure described in Example 6.

EXAMPLE 21

But-1-Ene Production from Butan-1-yl Sulfate with Purified Terpene Synthases The enzymatic assays are carried out under the following conditions:
50 mM Tris-HCl pH 7.5
50-100 mM $MgCl_2$
20-50 mM KCl
2-5 mM DTT
50 mM butan-1-yl sulfate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. But-1-ene production is analyzed using the GC/FID procedure described in Example. 8

EXAMPLE 22

But-1-Ene and but-2-Ene Production from Butan-2-yl Sulfate with Purified Terpene Synthases The enzymatic assays were carried out under the following conditions:
50 mM Tris-HCl pH 7.5
50-100 mM $MgCl_2$
20-50 mM KCl
2-5 mM DTT
50 mM butan-2-yl sulfate
5 mg of the terpene synthase is added to 0.5 ml of reaction mixture. An enzyme-free control reaction is carried out in parallel. Assays are incubated at 37° C. for 24-48 hours in a 1.5 ml sealed glass vial (Interchim) with shaking. But-1-ene and but-2-ene production is analyzed using the GC/FID procedure described in Example 9.

EXAMPLE 23

Propylene Production from Propan-2-yl Diphosphate Using Purified Prenyltransferase Enzyme catalyzed conversion of propan-2-yl diphosphate into propylene is carried out under the following conditions:
50 mM Tris-HCl pH 7.5
20 mM propan-2-yl diphosphate
33 mM KCl
33 mM $MgCl_2$
4 mM DTT
The reaction is started by adding 3 mg of the preparation of prenyltransferase to 0.5 ml of reaction mixture.
Assays are incubated with shaking at 37-42° C. for 2-72 h in 1.5 ml sealed glass vials (Interchim). Propylene production is analyzed using GC/FID procedure described in Example 2.

EXAMPLE 24

Propylene Production from Propan-2-yl Monophosphate Using Purified Prenyltransferase Enzyme catalyzed conversion of propan-2-yl monophosphate into propylene is carried out under the following conditions:
50 mM Tris-HCl pH 7.5
20 mM propan-2-yl monophosphate
33 mM KCl
33 mM $MgCl_2$
4 mM DTT
The reaction is started by adding 3 mg of the preparation of prenyltransferase to 0.5 ml of reaction mixture.
Assays are incubated with shaking at 37-42° C. for 2-72 h in 1.5 ml sealed glass vials (Interchim). Propylene production is analyzed using GC/FID procedure described in Example 2.

EXAMPLE 25

Propylene Production from Propan-2-yl Sulfate Using Purified Prenyltransferase Enzyme catalyzed conversion of propan-2-yl sulfate into propylene is carried out under the following conditions:
50 mM Tris-HCl pH 7.5
20 mM propan-2-yl sulfate
33 mM KCl
33 mM $MgCl_2$
4 mM DTT
The reaction is started by adding 3 mg of the preparation of prenyltransferase to 0.5 ml of reaction mixture.
Assays are incubated with shaking at 37-42° C. for 2-72 h in 1.5 ml sealed glass vials (Interchim). Propylene production is analyzed using GC/FID procedure described in Example 2.

EXAMPLE 26

Isobutene Production from 1,1-Dimethylethyl Diphosphate Using Purified Prenyltransferase Enzyme catalyzed conversion of 1,1-dimethylethyl diphosphate into isobutene is carried out under the following conditions:
50 mM Tris-HCl pH 7.5
20 mM 1,1-dimethylethyl diphosphate
33 mM KCl
33 mM $MgCl_2$
4 mM DTT The reaction is started by adding 3 mg of the preparation of prenyltransferase to 0.5 ml of reaction mixture.

Assays are incubated with shaking at 37-42° C. for 2-72 h in 1.5 ml sealed glass vials (Interchim). Isobutene production is analyzed using GC/FID procedure described in Example 6.

EXAMPLE 27

Isobutene Production from 1,1-Dimethylethyl Monophosphate Using Purified Prenyltransferase Enzyme catalyzed conversion of 1,1-dimethylethyl monophosphate into isobutene is carried out under the following conditions:
50 mM Tris-HCl pH 7.5
20 mM 1,1-dimethylethyl monophosphate
33 mM KCl
33 mM $MgCl_2$
4 mM DTT The reaction is started by adding 3 mg of the preparation of prenyltransferase to 0.5 ml of reaction mixture.

Assays are incubated with shaking at 37-42° C. for 2-72 h in 1.5 ml sealed glass vials (Interchim). Isobutene production is analyzed using GC/FID procedure described in Example 6.

EXAMPLE 28

Isobutene Production from 1,1-Dimethylethyl Sulfate Using Purified Prenyltransferase Enzyme catalyzed conversion of 1,1-dimethylethyl sulfate into isobutene is carried out under the following conditions:
50 mM Tris-HCl pH 7.5
20 mM 1,1-dimethylethyl sulfate
33 mM KCl
33 mM $MgCl_2$
4 mM DTT The reaction is started by adding 3 mg of the preparation of prenyltransferase to 0.5 ml of reaction mixture.

Assays are incubated with shaking at 37-42° C. for 2-72 h in 1.5 ml sealed glass vials (Interchim). Isobutene production is analyzed using GC/FID procedure described in Example 6.

EXAMPLE 29

Isobutene Production from 2-Methylpropan-1-yl Diphosphate Using Purified Prenyltransferase Enzyme catalyzed conversion of 2-methylpropan-1-yl diphosphate into isobutene is carried out under the following conditions:
50 mM Tris-HCl pH 7.5
20 mM 2-methylpropan-1-yl diphosphate
33 mM KCl
33 mM $MgCl_2$
4 mM DTT The reaction is started by adding 3 mg of the preparation of prenyltransferase to 0.5 ml of reaction mixture.

Assays are incubated with shaking at 37-42° C. for 2-72 h in 1.5 ml sealed glass vials (Interchim). Isobutene production is analyzed using GC/FID procedure described in Example 6.

EXAMPLE 30

Isobutene Production from 2-Methylpropan-1-yl Monophosphate Using Purified Prenyltransferase Enzyme catalyzed conversion of 2-methylpropan-1-yl monophosphate into isobutene is carried out under the following conditions:
50 mM Tris-HCl pH 7.5
20 mM 2-methylpropan-1-yl monophosphate
33 mM KCl
33 mM $MgCl_2$
4 mM DTT The reaction is started by adding 3 mg of the preparation of prenyltransferase to 0.5 ml of reaction mixture.

Assays are incubated with shaking at 37-42° C. for 2-72 h in 1.5 ml sealed glass vials (Interchim). Isobutene production is analyzed using GC/FID procedure described in Example 6.

EXAMPLE 31

Isobutene Production from 2-Methylpropan-1-yl Sulfate Using Purified Prenyltransferase Enzyme catalyzed conversion of 2-methylpropan-1-yl sulfate into isobutene is carried out under the following conditions:
50 mM Tris-HCl pH 7.5
20 mM 2-methylpropan-1-yl sulfate
33 mM KCl
33 mM $MgCl_2$
4 mM DTT The reaction is started by adding 3 mg of the preparation of prenyltransferase to 0.5 ml of reaction mixture.

Assays are incubated with shaking at 37-42° C. for 2-72 h in 1.5 ml sealed glass vials (Interchim). Isobutene production is analyzed using GC/FID procedure described in Example 6.

---

The invention claimed is:

1. A method for producing a mono alkene, wherein the method comprises converting an alkyl monoester into a monoalkene by a terpene synthase (EC 4.2.3) or a prenyltransferase (EC 2.5.1) which enzymatically eliminates a molecule XH, wherein:

the alkyl monoester is a compound of formula (I)

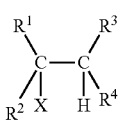

(I)

wherein $R^1$, $R^2$, $R^3$ and $R^4$ are each independently selected from (—H), methyl (—CH3) or ethyl (—C2H5); and wherein X is selected from:
O—PO$_3$H$_2$ monophosphate
O—PO$_2$H—O—PO$_3$H$_2$ diphosphate
O—SO$_3$H sulfate and wherein
the monoalkene is a compound of formula (II)

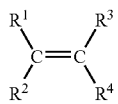

(II)

wherein $R^1$, $R^2$, $R^3$ and $R^4$ have the same meanings as defined for the compound of formula (I).

2. The method of claim 1 wherein the enzymatic elimination of the molecule XH is catalyzed by the terpene synthase (EC 4.2.3).

3. The method of claim 2 wherein the terpene synthase is an isoprene synthase (EC 4.2.3.27).

4. The method of claim 2 wherein the terpene synthase is a myrcene/ocimene synthase (EC 4.2.3.15).

5. The method of claim 2 wherein the terpene synthase is a farnesene synthase (EC 4.2.3.46 or EC 4.2.3.47).

6. The method of claim 2 wherein the terpene synthase is a pinene synthase (EC 4.2.3.14).

7. The method of claim 1 wherein the enzymatic elimination of the molecule XH is catalyzed by a prenyltransferase (EC 2.5.1).

8. The method of claim 1 wherein:
(i) the alkyl monoester is ethyl diphosphate and the monoalkene is ethylene; or
(ii) the alkyl monoester is propan-1-yl diphosphate (propyl diphosphate) and the monoalkene is methylethylene (propylene); or
(iii) the alkyl monoester is propan-2-yl diphosphate (isopropyl diphosphate) and the monoalkene is methylethylene (propylene); or
(iv) the alkyl monoester is butan-1-yl diphosphate (1-butyl diphosphate) and the monoalkene is but-1-ene; or
(v) the alkyl monoester is butan-2-yl diphosphate (2-butyl diphosphate) and the monoalkene is but-1-ene and but-2-ene; or
(vi) the alkyl monoester is 2-methylpropan-1-yl diphosphate (isobutyl diphosphate) and the monoalkene is 2-methylprop-1-ene (isobutene; isobutylene); or
(vii) the alkyl monoester is 1,1-dimethylethyl diphosphate (tert-butyl diphosphate) and the monoalkene is 2-methylprop-1-ene (isobutene; isobutylene); or
(viii) the alkyl monoester is ethyl monophosphate and the monoalkene is ethylene; or
(ix) the alkyl monoester is propan-1-yl monophosphate (propyl monophosphate) and the monoalkene is methylethylene (propylene); or
(x) the alkyl monoester is propan-2-yl monophosphate (isopropyl monophosphate) and the monoalkene is methylethylene (propylene); or
(xi) the alkyl monoester is butan-1-yl monophosphate (1-butyl monophosphate) and the monoalkene is but-1-ene; or
(xii) the alkyl monoester is butan-2-yl monophosphate (2-butyl monophosphate) and the monoalkene is but-1-ene and but-2-ene; or
(xiii) the alkyl monoester is 2-methylpropan-1-yl monophosphate (isobutyl monophosphate) and the monoalkene is 2-methylprop-1-ene (isobutene); or
(xiv) the alkyl monoester is 1,1-dimethylethyl monophosphate (tert-butyl monophosphate) and the monoalkene is 2-methylprop-1-ene (isobutene; isobutylene); or
(xv) the alkyl monoester is ethyl sulfate and the monoalkene is ethylene; or
(xvi) the alkyl monoester is propan-1-yl sulfate (propyl sulfate) and the monoalkene is methylethylene (propylene); or
(xvii) the alkyl monoester is propan-2-yl sulfate (isopropyl sulfate) and the monoalkene is methylethylene (propylene); or
(xviii) the alkyl monoester is butan-1-yl sulfate (1-butyl sulfate) and the monoalkene is but-1-ene; or
(xix) the alkyl monoester is butan-2-yl sulfate (2-butyl sulfate) and the monoalkene is but-1-ene and but-2-ene; or
(xx) the alkyl monoester is 2-methylpropan-1-yl sulfate (isobutyl sulfate) and the monoalkene is 2-methylprop-1-ene (isobutene; isobutylene); or
(xxi) the alkyl monoester is 1,1-dimethylethyl sulfate (tert-butyl sulfate) and the monoalkene is 2-methylprop-1-ene (isobutene; isobutylene).

9. The method of claim 1 wherein the method is carried out in the presence of a microorganism expressing an enzyme selected from a terpene synthase, an isoprene synthase (EC 4.2.3.27), a myrcene/ocimene synthase (EC 4.2.3.15), a farnesene synthase (EC 4.2.3.46 or EC 4.2.3.47), a pinene synthase (EC 4.2.3.14), a monoterpene synthase, or a prenyltransferase (EC 2.5.1).

10. The method of claim 9 wherein the microorganism is furthermore capable of producing the alkyl monoester to be converted.

11. A recombinant microorganism genetically modified to produce an alkyl monoester and which overexpresses an enzyme capable of converting the alkyl monoester into a monoalkene by an enzymatic elimination of a molecule XH wherein:
the enzyme is a terpene synthase (EC 4.2.3) or a prenyltransferase (EC 2.5.1);
the alkyl monoester is a compound of formula (I)

wherein $R^1$, $R^2$, $R^3$ and $R^4$ are each independently selected from hydrogen, methyl or ethyl; and wherein X is selected from:
O—$PO_3H_2$ monophosphate
O—$PO_2H$—O—$PO_3H_2$ diphosphate
O—$SO_3H$ sulfate
and wherein
the monoalkene is a compound of formula (II)

wherein $R^1$, $R^2$, $R^3$ and $R^4$ have the same meanings as defined for the compound of formula (I).

12. The recombinant microorganism of claim 11, wherein the enzyme is a terpene synthase.

13. A composition comprising the recombinant microorganism of claim 12.

14. The recombinant microorganism of claim 12, wherein the terpene synthase is selected from an isoprene synthase (EC 4.2.3.27), a myrcene/ocimene synthase (EC 4.2.3.15), a farnesene synthase (EC 4.2.3.46 or EC 4.2.3.47), a pinene synthase (EC 4.2.3.14), or a monoterpene synthase.

15. The method of claim 1, wherein the method further comprises recovering the monoalkene.

16. The method of claim 9, wherein the method further comprises recovering the monoalkene.

17. The method of claim 10, wherein the method further comprises recovering the monoalkene.

18. The recombinant microorganism of claim 11, wherein the enzyme is a prenyltransferase (EC 2.5.1).

19. A composition comprising the recombinant microorganism of claim 18.

20. The method of claim 2 wherein the terpene synthase is a monoterpene synthase.

* * * * *